(12) United States Patent
Trollsas et al.

(10) Patent No.: US 8,425,587 B2
(45) Date of Patent: Apr. 23, 2013

(54) METHOD OF TREATMENT WITH A BIOABSORBABLE STENT WITH TIME DEPENDENT STRUCTURE AND PROPERTIES AND REGIO-SELECTIVE DEGRADATION

(75) Inventors: Mikael Trollsas, San Jose, CA (US);
Dariush Davalian, San Jose, CA (US);
Michael Huy Ngo, San Jose, CA (US);
Hao-Ming Hsiao, Cupertino, CA (US);
Boris Anukhin, San Jose, CA (US);
Syed F. A. Hossainy, Fremont, CA (US);
David C. Gale, Kennesaw, GA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 542 days.

(21) Appl. No.: 12/561,971

(22) Filed: Sep. 17, 2009

(65) Prior Publication Data
US 2011/0066225 A1    Mar. 17, 2011

(51) Int. Cl.
*A61F 2/82* (2006.01)
(52) U.S. Cl.
USPC .................................... 623/1.16; 623/1.38
(58) Field of Classification Search ............... 623/1.38, 623/1.13–1.16; 606/108, 198; 424/426
See application file for complete search history.

(56) References Cited

U.S. PATENT DOCUMENTS

| 5,486,546 | A | 1/1996 | Mathiesen et al. |
| 5,707,385 | A | 1/1998 | Williams |
| 5,919,893 | A | 7/1999 | Roby et al. |
| 5,972,027 | A | 10/1999 | Johnson |
| 6,174,329 | B1 | 1/2001 | Callol et al. |
| 6,258,117 | B1* | 7/2001 | Camrud et al. ............... 623/1.16 |
| 7,169,178 | B1 | 1/2007 | Santos et al. |
| 7,175,873 | B1 | 2/2007 | Roorda et al. |
| 7,294,146 | B2* | 11/2007 | Chew et al. .................. 623/1.12 |
| 7,357,942 | B2* | 4/2008 | Burke et al. .................. 424/423 |
| 7,625,401 | B2* | 12/2009 | Clifford et al. ............... 623/1.38 |
| 2001/0044651 | A1* | 11/2001 | Steinke et al. ............... 623/1.16 |
| 2002/0065553 | A1 | 5/2002 | Weber et al. |
| 2002/0111590 | A1 | 8/2002 | Davila et al. |
| 2003/0040771 | A1* | 2/2003 | Hyodoh et al. ............... 606/200 |
| 2003/0040772 | A1 | 2/2003 | Hyodoh et al. |
| 2003/0083740 | A1 | 5/2003 | Pathak |
| 2003/0181973 | A1 | 9/2003 | Sahota |
| 2003/0199969 | A1* | 10/2003 | Steinke et al. ............... 623/1.16 |
| 2004/0034409 | A1 | 2/2004 | Heublein et al. |

(Continued)

FOREIGN PATENT DOCUMENTS
JP     2003-251680     9/2003

OTHER PUBLICATIONS

Loo et al., "Radiation effects on poly(lactide-co-glycolide) and poly-l-lactide", Polymer degradation and stability vol. 83, pp. 259-265 (2005).

(Continued)

*Primary Examiner* — Elizabeth Houston
(74) *Attorney, Agent, or Firm* — Squire Sanders (US) LLP

(57) ABSTRACT

A bioabsorbable polymeric stent with time dependent structure and properties and methods of treating a diseased blood vessel with the bioabsorable polymeric stent are disclosed. The structure and properties of the stent change with time and allow the vessel to be restored to a natural unstented state. The bioabsorbable stent loses mechanical integrity in a controlled manner due to modification of selected structural elements.

1 Claim, 12 Drawing Sheets

U.S. PATENT DOCUMENTS

| | | |
|---|---|---|
| 2004/0093077 A1 | 5/2004 | White et al. |
| 2004/0147998 A1 | 7/2004 | Nolting |
| 2005/0033399 A1 | 2/2005 | Richter |
| 2005/0125051 A1* | 6/2005 | Eidenschink et al. ....... 623/1.12 |
| 2005/0182479 A1* | 8/2005 | Bonsignore et al. ......... 623/1.15 |
| 2006/0034888 A1 | 2/2006 | Pacetti et al. |
| 2006/0122691 A1 | 6/2006 | Richter |
| 2006/0217795 A1 | 9/2006 | Besselink et al. |
| 2007/0219612 A1 | 9/2007 | Andreas et al. |
| 2007/0219642 A1 | 9/2007 | Richter |
| 2007/0254012 A1 | 11/2007 | Ludwig et al. |
| 2007/0299510 A1 | 12/2007 | Venkatraman et al. |
| 2008/0058919 A1* | 3/2008 | Kramer-Brown et al. ... 623/1.34 |
| 2009/0246253 A1* | 10/2009 | Ding ............................. 424/426 |
| 2010/0070024 A1* | 3/2010 | Venturelli et al. ........... 623/1.22 |

OTHER PUBLICATIONS

Yoshioka et al., "Drug release from pol(d-l-lactide) microspheres by gamma irradiation", J. of controller release vol. 37, pp. 263-267 (1995).

* cited by examiner

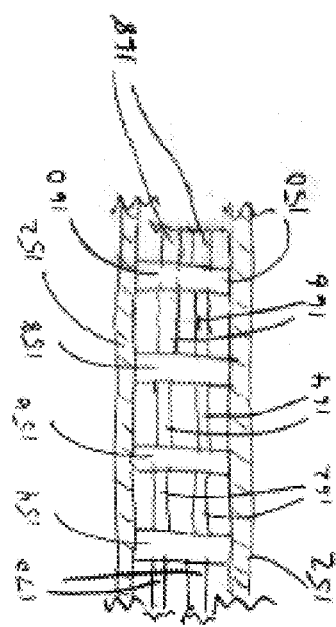
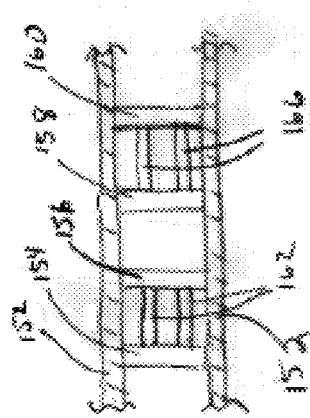
FIG. 3A
FIG. 3B

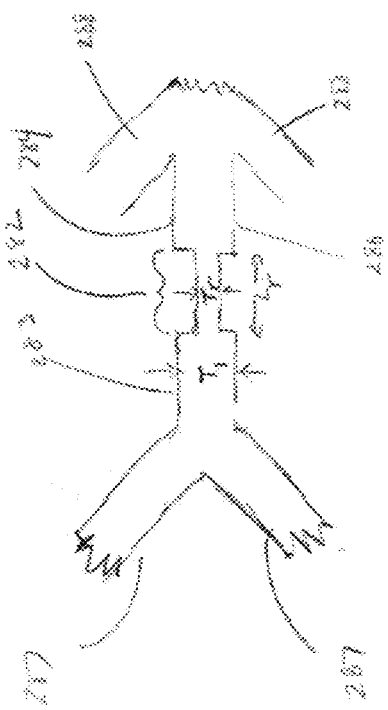
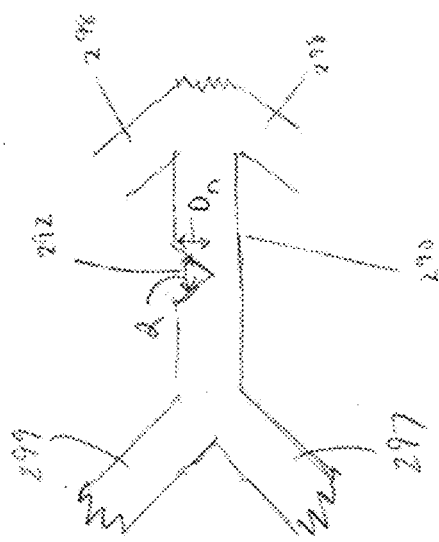
FIG. 10A
FIG. 10B

METHOD OF TREATMENT WITH A BIOABSORBABLE STENT WITH TIME DEPENDENT STRUCTURE AND PROPERTIES AND REGIO-SELECTIVE DEGRADATION

BACKGROUND OF THE INVENTION

1. Field of the Invention

This invention relates to methods of treatment of blood vessels with bioabsorbable polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug by incorporating a drug through the scaffolding material.

The stent must be able to satisfy a number of mechanical requirements. The stent must be have sufficient radial strength so that it is capable of withstanding the structural loads, namely radial compressive forces, imposed on the stent as it supports the walls of a vessel. This structural load will change as a function of time as the vessel heals, positively remodeling or adapting to the presence of the stent.

Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents made from biostable or non-erodible materials, such as metals, have become the standard of care for percutaneous coronary intervention (PCI) as well as in peripheral applications, such as the superficial femoral artery (SFA), since such stents have been shown to be capable of preventing early and later recoil and restenosis. For a variety of reasons, the performance of stents in the SFA appear to be more problematic than in coronary vessels and in other peripheral vascular beds, such as the iliac and carotid arteries. This may be due to the significant mechanical stresses placed on the devices in the dynamic SFA environment relative to other vasculature, as well as the vessel length and the severity of stenotic and occlusive disease. The SFA is subjected to various forces, such as compression, torsion, flexion, extension, and contraction, which place a high demand on the mechanical performance of implants.

However, a stent made out of such biostable material tends to retain mechanical or structural integrity and remains at the implant site indefinitely unless it is removed by intervention or is dislodged. Intervention presents risks to the patient and dislodgement can have significant adverse consequences on the patient. Leaving the stent at the implant site permanently also has disadvantages. One disadvantage is that the stented segment has the compliance of the stent which is very different from that of healthy vessel segment. Another drawback of such durably implanted stents is that the permanent interaction between the stent and surrounding tissue can pose a risk of endothelial dysfunction and late thrombosis.

SUMMARY OF THE INVENTION

Various embodiments of the present invention include a stent for treating a diseased section of a blood vessel, comprising: a bioabsorbable polymeric scaffolding composed of a pattern of struts, the pattern including a plurality of cylindrical rings connected by linking struts, wherein each of the linking struts between at least one set of adjacent rings comprises a coating material above at least a portion of the linking struts that is different from the ring struts, and wherein the coating material accelerates degradation of the linking struts and causes the linking struts to break before the rings of the scaffolding when the stent is deployed in a living body.

Additional embodiments of the present invention include a stent for treating a diseased section of a blood vessel, comprising: a bioabsorbable polymeric scaffolding composed of a pattern of struts, the pattern including a plurality of cylindrical rings connected by linking struts, wherein the scaffolding polymer of a region of each of the linking struts between at least one set of adjacent rings has a lower Mw or Mn than the scaffolding polymer outside of the region, wherein the lower Mw or Mn causes the linking strut to break before the rings of the scaffolding when the stent is deployed in a living body.

Further embodiments of the present invention include a method of making a stent, comprising: providing a bioabsorbable polymeric scaffolding composed of a pattern of struts, the pattern including a plurality of cylindrical rings connected by linking struts; and applying a coating selectively to a region of at least one of the linking struts between at least one set of adjacent rings, wherein the coating induces chemical degradation of the scaffolding polymer in the region which lowers the Mw or Mn of the scaffolding polymer in the region, and wherein the lower Mw or Mn reduces the tensile strength, strain to failure, and fracture resistance of the region that causes the one or more linking struts to break prematurely as compared to the remainder of the scaffolding when the stent is deployed in a living body.

Other embodiments of the present invention include a method of making a stent, comprising: providing a bioabsorbable polymeric scaffolding composed of a pattern of struts, the pattern including a plurality of cylindrical rings connected by linking struts; and selectively modifying a region of at least one of the linking struts between at least one set of adjacent rings, wherein the modification is selected from the group consisting of exposure to radiation in the IR to UV wavelength, exposure to e-beam radiation, exposure to gamma radiation, exposure to neutron bombardment, exposure to reactive ion etching, exposure to plasma, direct heating, and exposure to ultrasound frequency application, wherein the modification induces chemical degradation of the scaffolding polymer in the region which lowers the Mw or Mn of the scaffolding polymer in the region, and wherein the lower Mw or Mn reduces the tensile strength, strain to failure, and fracture resistance of the region that causes the one or more linking struts to break prematurely as compared to the remainder of the scaffolding when the stent is deployed in a living body.

Further embodiments of the present invention include a stent for treating a diseased section of a blood vessel, comprising: a bioabsorbable polymeric scaffolding composed of a pattern of struts, the pattern comprising a first axial section and a second axial section, wherein the first axial section comprises a first set of cylindrical rings each connected by a set of linking struts and the second axial section comprises a second set of cylindrical rings each connected by a set of linking struts, wherein the first axial section and the second axial section are connected by a set of modified linking struts, wherein each of the modified linking struts comprises a structural feature different from the linking struts in the first and second axial sections, and wherein the structural feature induces failure of the modified linking struts before the linking struts in the first and second axial sections after deployment in a living body resulting in disconnecting of the first and second axial sections.

Additional embodiments of the present invention include a method of treating a diseased section of a blood vessel, comprising: deploying a bioabsorbable polymeric stent to a deployment diameter at a diseased section of a blood vessel to form a stented segment of the vessel comprising the stent and the vessel wall, the stent comprising a scaffolding composed of a pattern of struts, the pattern comprising a plurality of cylindrical rings connected by linking struts, wherein selected linking struts break resulting in at least one ring or at least one group of consecutive rings being disconnected from adjacent rings, and wherein the at least one ring or the group of rings remain structurally intact after the selected linking struts break.

DETAILED DESCRIPTION OF THE INVENTION

Coronary arteries refer generally to arteries that branch off the aorta to supply the heart muscle with oxygenated blood. Peripheral arteries refer generally to blood vessels outside the heart and brain.

In both coronary artery disease and peripheral artery disease, the arteries become hardened and narrowed or stenotic and restrict blood flow. In the case of the coronary arteries, blood flow is restricted to the heart, while in the peripheral arteries blood flow is restricted leading to the kidneys, stomach, arms, legs and feet. The narrowing is caused by the buildup of cholesterol and other material, called plaque, on their inner walls of the vessel. Such narrowed or stenotic portions are often referred to as lesions. Artery disease also includes the reoccurrence of stenosis or restenosis that occurs after an angioplasty treatment. Although there are probably several mechanisms that lead to restenosis of arteries, an important one is the inflammatory response, which induces tissue proliferation around an angioplasty site. The inflammatory response can be caused by the balloon expansion used to open the vessel, or if a stent is placed, by the foreign material of the stent itself.

Embodiments of the present invention are applicable to endovascular treatment of coronary and peripheral disease in coronary arteries and various peripheral vessels including the superficial femoral artery, the iliac artery, and carotid artery. The embodiments are further applicable to various stent types, such as self-expandable and balloon expandable stents. The embodiments are further applicable to various stent designs including scaffolding structures formed from tubes, wire structures, and woven mesh structures.

In embodiments of the present invention, a stent includes a plurality of cylindrical rings connected or coupled with linking elements. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are non-load bearing, serving to maintain connectivity between the rings. For example, a stent may include a scaffolding composed of a pattern or network of interconnecting structural elements or struts.

Figure 1:
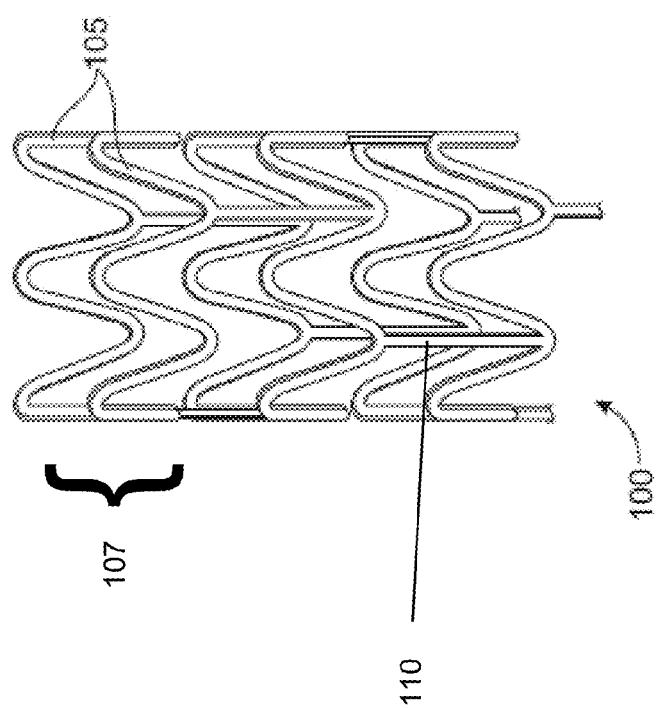
FIG. 1 depicts an exemplary stent.

FIG. 1 depicts a view of an exemplary stent 100. In some embodiments, a stent may include a body, backbone, or scaffolding having a pattern or network of interconnecting structural elements 105. Stent 100 may be formed from a tube (not shown). FIG. 1 illustrates features that are typical to many stent patterns including cylindrical rings 107 connected by linking elements 110. As mentioned above, the cylindrical rings are load bearing in that they provide radially directed force to support the walls of a vessel. The linking elements generally function to hold the cylindrical rings together. The stent 100 includes bending elements composed of, for example, struts 112A and 112B that are joined at an apex or a crown 114. When stent 100 is expanded to a deployed or deployment diameter, struts 112A and 112B bend resulting in plastic deformation at apex 114.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped on to a balloon or catheter for delivery into a bodily lumen.

The intent of the treatment of artery disease with nonerodible or biostable metallic stents with drug-eluting polymer coatings is to heal a vessel and prevent restenosis. However, after the vessel is healed, a stiff metallic structure is left behind which alters the compliance of the vessel permanently. Specifically, the permanent structure inhibits or prevents the natural pulsatile movement or flexing of a vessel. Alternatively, a compliant nonerodible metallic stent can be made out of spring-like material, such as a nickel-titanium alloy. While these stents allow some flexing of the vessel, a permanent metallic structure is still left behind whose properties do not change over time, even though the cardiac demands do change over time in the short and long term. Additionally the presence of the permanent structure also present risks such as thrombosis.

The various embodiments of the present invention include a bioabsorbable polymeric stent, its design and fabrication, and treatment of a vessel with the stent. In such embodiments, the bioabsorbable stent has time dependent structure and properties that enable the compliance of a stented segment to change with time. The compliance converges to that of or close to the natural compliance of a healthy vessel that is free of a stent. The healed vessel has increased dimensions and exhibits pulsatile motion.

Stented segment refers to the composite structure that includes the deployed stent and the vessel wall. The compliance of a segment of a vessel refers to the change in luminal area per unit change in pressure in the vessel. The time dependent behavior enables the stent to change according to the requirements of the vessel and to disappear from the implant region leaving a healed vessel that is free of a permanent artificial structure or material.

In embodiments of the present invention, the bioabsorbable stent is deployed at a diseased section of a vessel. The deployed stent expands the diseased section to a deployment diameter to form a stented segment. The initial clinical need for any stent is to provide mechanical support to maintain patency or keep a vessel open at or near the deployment diameter. The stent is designed, as described below, to have sufficient radial strength to maintain such patency for a period of time.

The patency provided by the stent allows the stented segment of the vessel to undergo remodeling at the increased diameter. Remodeling refers generally to structural changes in the vessel wall that enhance its load-bearing ability. The high radial strength of the stent tends to freeze the size of the vessel a period of time to enable remodeling at the increased size. During this time period, the stent inhibits or prevents the natural pulsatile function of the vessel.

The stent structure prevents recoil and maintains a circular lumen while the vessel remodels and molds itself to the stented diameter, which corresponds to positive remodeling. Early recoil before sufficient modeling takes place can result in negative remodeling, referring to molding of the stent to a diameter significantly less than the original stented diameter.

A period of patency is required in order to obtain permanent positive remodeling. However, the vessel requires the patency for only a finite time to obtain such positive remodeling. As the polymer of the stent degrades, the radial strength of the stent decreases and the load of the vessel is gradually transferred from the stent to the remodeled vessel wall. Remodeling of the vessel wall can continue even after loss of radial strength of the stent.

The drop in radial strength is not necessarily due to fracture or breaking of the stent scaffolding. For example, for a stent scaffolding, such as that in FIG. 1, the radial strength loss is preferably due to degradation of strength of the polymer in the bending regions. The molecular weight of the polymer in these regions degrades and eventually the polymer is unable to oppose the inwardly directed force imposed by the vessel wall. The degradation of the molecular weight of the polymer leads to a loss in strength. The stent scaffolding then exhibits a controlled loss in radial strength. Controlled loss of radial strength refers to the loss without dislodgement of particulate material that can cause thrombo-embolitic events. Decline in radial strength due to fracture or breaking of the stent scaffolding can lead to such dislodgement.

In addition to the decline in radial strength, the degradation of the stent also causes a gradual decline in the mechanical integrity. Mechanical integrity refers to the connectivity of struts and the size and shape of the overall stent structure. The stent may be designed to lose mechanical integrity in a controlled manner that avoids dislodgement of stent material which can cause thrombo-embolitic events. In some embodiments, non-load bearing members are designed to fracture and break before load-bearing members. In such embodiments, non-load bearing members are selectively modified to induce such failure.

The decline in mechanical integrity is also accompanied by mass loss. Eventually the stent disappears completely from the stented segment, leaving a healed vessel. The gradual transfer of load through controlled loss of radial strength, controlled loss of mechanical integrity, and loss of mass allows the gradual restoration of the natural physiological function of the vessel including the restoration of the pulsatile function of the vessel.

It is important to note that the treatment by the stent of the present invention and the healing result is not an inherent result of treatment with any stent made from a bioabsorbable material. The time dependent structure and property behavior of the stent including: radial strength to support a vessel for a sufficient time to provide positive remodeling, controlled loss of radial strength, controlled and gradual loss mechanical integrity, and complete mass loss; are a result of several design inputs of the stent described below that are essential to the behavior.

The compliance of a stented segment is time dependent due to the time dependent structure and properties of the bioabsorbable stent. The compliance of a stented segment is the compliance of the composite structure that includes both the stent and the vessel. In the absence of a stent, the segment has the compliance of the vessel wall. The change in the compliance is due also to remodeling of the vessel wall.

The compliance of the stented segment gradually converges to the natural compliance of a vessel as the radial strength declines, mechanical integrity declines, and mass is lost from the stent. A decline of radial strength, mechanical integrity, or both are accompanied by the gradual increase in flexing or pulsatile motion in the vessel. Thus, the vessel wall is remodeling while it is in motion and the compliance increases to that of healed vessel and is free to change according to the requirements of the vessel.

Since the compliance of the stented segment converges to that of the natural compliance of the vessel, the difference in compliance between the stent and the vessel, or compliance mismatch is reduced as the stent degrades. Compliance mismatch in the treatment with metallic stents has been identified as a contributor to the process of restenosis and potentially late adverse events. [Do we have reference for this?]

The time dependent structure and property design of the stent of the present invention also provides optimal scaffolding performance between two extremes of total compliance mismatch from a metallic stent on the one hand and abrupt reclosure of the vessel from balloon angioplasty on the other hand. The reduction in compliance mismatch occurs both in the stented length and at the ends.

Another advantage of the bioabsorbable stent and treatment is the restoration of the natural pulsatile function of the vessel. This potentially removes another source of irritation of the vessel. With a metallic stent, as the vessel tries to change diameter in response to the natural fluctuation in pressure within the vessel, the presence of a rigid stent will result in irritation and the potential inflammation of the vessel. The stent of the present invention gradually loses its rigidity and becomes flexible which removes this source of irritation. The stent can flex in response to fluctuations in pressure within the vessel. The complete absorption of the stent removes this source of irritation over the long term.

Additionally, the treatment described with the bioabsorbable stent can result in positive remodeling after the stent loses mechanical strength. The diameter and vessel area may decrease after the radial strength declines. However, as indicated, the remodeling process can continue. As the mechanical integrity declines, the vessel positively remodels to an increased vessel diameter and area. This has been observed in clinical trial results using a poly(L-lactide) stent. Lancet.com Vol. 373 Mar. 14, 2009. A metal stent, on the other hand, will freeze the vessel at the initial diameter of the stent or, if the stent recoils, to whatever diameter to which the stent recoils. If positive remodeling occurs in a treatment with a metal stent, a second intervention is often required to expand the metal stent to the new vessel diameter. With a bioabsorbable stent the stent can adjust to the new diameter of the vessel without the need for a second intervention.

Additionally, the bioabsorbable stent can include a polymer drug release coating. The coating can include a bioabsorbable polymer mixed with an antiproliferative drug for the control of smooth muscle cell proliferation (SMP). SMP is a biological response of the vessel and is part of the remodeling process. However, if it is not controlled, SMP can cause restenosis. The stent of the present invention is designed to provide a release profile which controls proliferation during smooth muscle cell proliferation, but terminates soon enough to allow complete or almost complete endothelialization of stent struts prior to substantial mass loss and mechanical integrity loss. "Almost complete" can correspond to at least 90% of struts covered by an endothelial layer. Specifically, the stent is designed to have a drug release profile that declines to zero between 3-4 months after intervention.

Endothelialization is an important part of the healing process with a bioabsorbable stent. Both the degree of endothelialization and timing of the endothelialization with respect to the other stent behavior are important features. Endothelialization refers to coverage of a surface with endothelial tissue or endothelial cells. Complete or almost complete endothelialization of the vessel wall and stent struts is essential to prevent thrombosis associated with blood contacting stent surfaces, incomplete strut apposition (persistent or late-acquired), and dislodgement of particulate stent material. Additionally, the timing of the endothelialization with respect to mechanical integrity loss and mass loss is also an important aspect of the healing process.

The presence of a blood-contacting surface of a foreign body regardless of the level of hemo-compatibility presents a risk of thrombosis. In general, endothelialization plays a crucial role in reducing or preventing vascular thrombosis and intimal thickening. Specifically, the endothelial coverage reduces or prevents deposition of proteins on the vessel wall or stent struts. Such deposition can contribute to or increase risk of thrombosis. Therefore, early and complete endothelialization of the vessel wall and stent are essential. The stent is designed to allow for complete or almost complete endothelialization of stent struts between 4 and 6 months after deployment. Such a range can be achieved through the use of small enough strut dimensions (e.g., a cross-section of 150× 150 microns), a biocompatible scaffolding material such as a biodegradable polyester, and a drug release profile that provides complete release by about 4 months.

As discussed above, the time dependent structure and property behavior of the bioabsorbable stent requires a gradual transfer of load through loss of radial strength and decline of mechanical integrity to provide healing of the vessel. Embodiments of the present invention include mechanisms by which the stent can exhibit such behavior. In particular, these mechanisms include the relative timing of decline of radial strength, decline of mechanical integrity, and endothelialization. These embodiments also include the manner of loss of mechanical integrity. The bioabsorable stent is designed to exhibit such mechanisms.

The structure and properties that change over time correspond to several parameters. Structure and properties refer generally to mechanical properties and microstructure of the polymer. These include creep compliance, extent of plastic deformation, internal time constant and subsequently the Deborah number, degree of plasticization and subsequently glass transition temperature (Tg), extent of orientation, degree and orientation of crystalline domains, and strength and fracture toughness.

Strength and fracture toughness: Both the strength and fracture toughness deteriorate as the polymer degrades. The chemical hydrolysis reactions decrease the molecular weight of the polymer which decreases the strength.

Creep is the progressively increase in strain over a period of time of a polymer when subjected to a continuously applied stress. Creep compliance is the time dependent ratio of strain to stress during creep.

Extent of plastic deformation: For a balloon-expandable stent, as the high strain bending regions degrade, the regions lose strength and regions bend inward which results in a loss of plastic deformation.

Deborah number is defined as the ratio of a relaxation time, characterizing the intrinsic fluidity of a material, and the characteristic time scale of an experiment. In particular, the Deborah number, $D=W \times Tp$, where $W=2 \times \Pi \times$ frequency of external force application; Tp=Ratio of internal material viscosity/material modulus.

The Deborah number will increase if the frequency of the experimental perturbation is high. Alternatively, if the temperature of the material is low the viscosity of the dashpot behavior of the materials is high and the elastomeric modulus is low, both contributing to an increase in the Deborah number. However Deborah number can be decreased by increasing the crystallinity, thereby increasing the modulus. Increasing the amorphous molecular weight (e.g., Mn or Mw) of a polymer, hence the entanglement length of the polymer, will increase the Deborah number.

Degree of plasticization and subsequently Tg: As the stent polymer degrades, the Tg of the polymer will drop as molecular weight drops. Additionally, as the stent polymer degrades the molecular weight of the polymer will drop and the degree of crystallinity increases. This will lead to a loss of mechanical properties including fracture toughness.

Extent of orientation of polymer chains: Polymer chain orientation induced in the hoop direction increases the radial strength and fracture toughness. As the polymer degrades, the chains become shorter so strength and fracture toughness imparted to stent through orientation decreases.

Degree and orientation of crystalline domains: As the polymer degrades the crystal domains become weaker and erode so that the strength and fracture toughness imparted to the polymer through orientation decreases.

In one set of embodiments, the bioabsorbable polymeric stent has a relatively high fracture toughness and has a high resistance to fracture. The stent is deployed to a diameter in a vessel segment and provides patency to the segment. In such embodiments, the mechanical integrity of the stent or portions thereof remain intact until the struts are covered or incorporated into the vessel wall by endothelial tissue.

In one embodiment, all or substantially all of the structural elements of a stent are completely covered by the endothelial tissue before the structural elements start to fail or break apart. In other embodiments, a structural element does not fail until incorporated and may fail before other structural elements that are not yet incorporated. In some embodiments, failure of a structural element refers to fractures without breaking apart completely. Alternatively, failure corresponds to the breaking apart of a structural element. In exemplary embodiments, the stent structure is completely or substantially covered or incorporated into the vessel wall in about 4 to 6 months, wherein substantially covered refers to at least 90% of struts covered.

Additionally, in these embodiments, radial strength can be lost before the complete or substantial endothelialization and failure of the stent. In such embodiments, the radial strength decline is not associated or due to breaking apart of the structural elements. Radial strength declines due to decrease in strength of the polymer arising from molecular weight degradation. In exemplary embodiments, the radial strength of the stent supports the vessel wall for between about 1 to 4 months.

In these embodiments, the particular structural elements or types of structural elements can be designed to fail before others. In one embodiment, linking elements between rings of a stent structure can fail resulting in partial or complete loss of connectivity between adjacent cylindrical rings. The cylindrical rings can remain intact for a period of time and maintain a circular shape. The cylindrical rings are decoupled which allows flexing or pulsatile motion of the stented vessel. A decoupled ring refers to a ring that is not connected to another ring by a linking elements.

In another set of embodiments, the bioabsorbable polymeric stent has a high radial strength that allows the stent to maintain patency after the stent structure begins to lose mechanical integrity. In these embodiments, the stent structure may be susceptible to fracture and breaking in selected structural elements or types thereof.

In some embodiments, the initial loss in mechanical integrity occurs at linking elements. In one embodiment, the linking elements between rings of a stent structure can fail which results in partial or complete loss of connectivity between adjacent cylindrical rings. The decoupled rings retain sufficient radial strength to support the vessel at or near the deployed diameter.

In certain embodiments, the rings are not covered or are only partially covered by endothelial tissue when mechanical integrity starts to fail. The rings can be covered by endothelial tissue after mechanical integrity starts to fail or, specifically, after the rings become decoupled due to failure of the linking elements. In other embodiments, the rings may be completely covered or incorporated by an endothelial layer before mechanical integrity starts to fail. In this second set of embodiments, decoupled rings continue to provide patency to the lumen, while in the above set of embodiments, the decoupled rings do not since the radial strength has already declined when the stent starts to lose mechanical integrity. In exemplary embodiments, the rings can be designed to maintain radial strength between about 1 to 4 months.

Figure 2A:
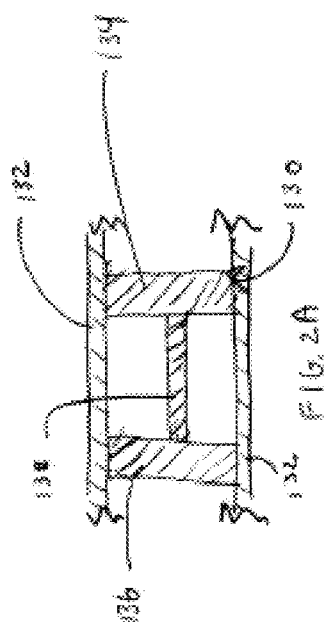
FIGS. 2A-C illustrate the failure of linking elements of a stent pattern which are applicable to both sets of embodiments discussed above.
Figure 2B:
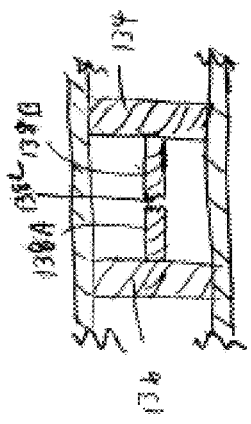
Figure 2C:
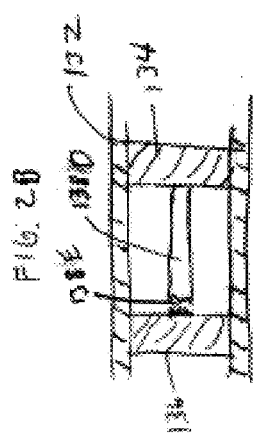

FIGS. 2A-C illustrate the failure of linking elements of a stent pattern which are applicable to both sets of embodiments discussed above. FIGS. 2A-C depict a two-dimensional projection of a stent 130 deployed in a segment of a vessel with walls 132. Stent 130 has rings 134 and 136 that are opposed against wall 132. The structure of rings 134 and 136 is not shown. Rings 134 are connected by linking elements which are exemplified by linking element 138.

FIG. 2B depicts failure of linking element 138 which has broken apart at point 138C into fragments 138A and 138B. FIG. 2C depicts failure of linking element 138 broken into fragment 138D at point 138E, the intersection of ring 136 and linking element 138.

In some embodiments, some or all of the rings can be decoupled from one another. In one embodiment, all of the rings are decoupled. In another embodiment, pairs or triples of rings remain coupled and are decoupled from adjacent single rings, ring pairs, or ring triples.

Figure 3A:
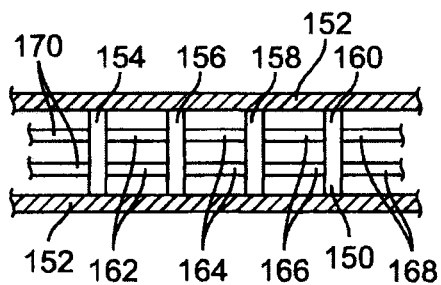
FIG. 3A depicts a two-dimensional projection of a stent with rings connected by linking elements deployed in a segment of a vessel.
Figure 3B:
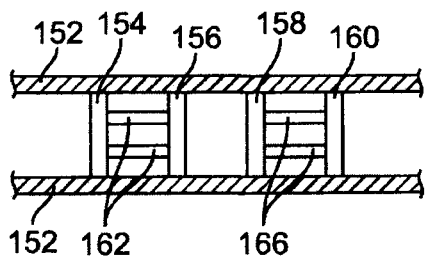
FIG. 3B depicts the stent of FIG. 3A with two disconnected ring pairs that are disconnected due to failure of linking elements between the pairs.
Figure 4:
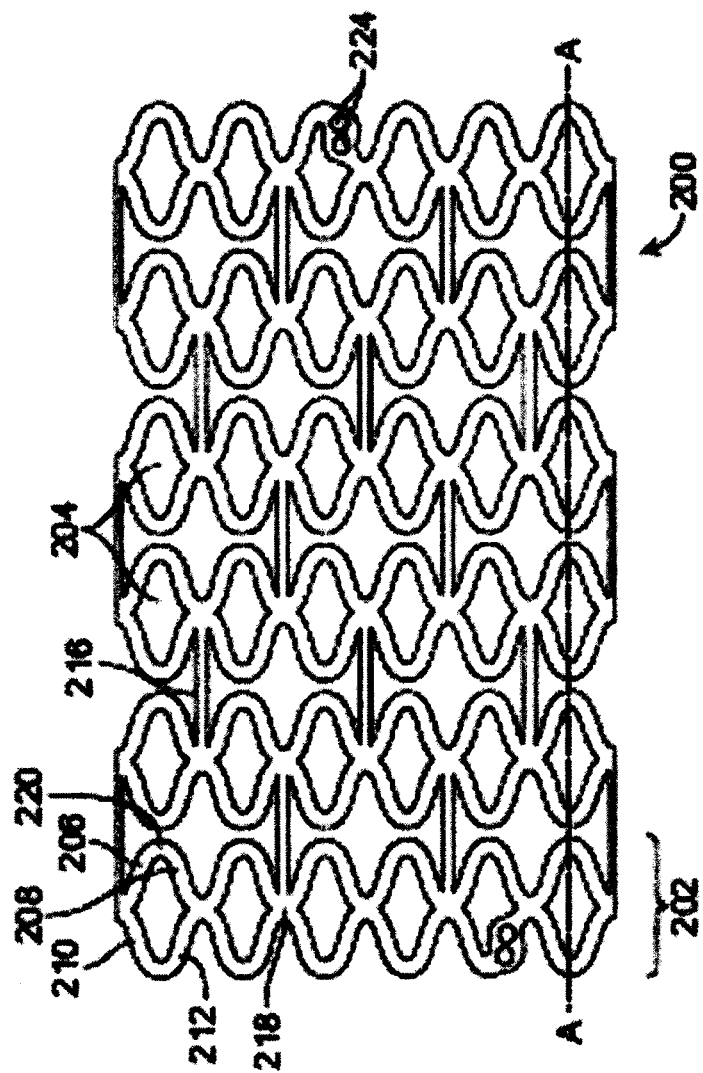
Figure 5:
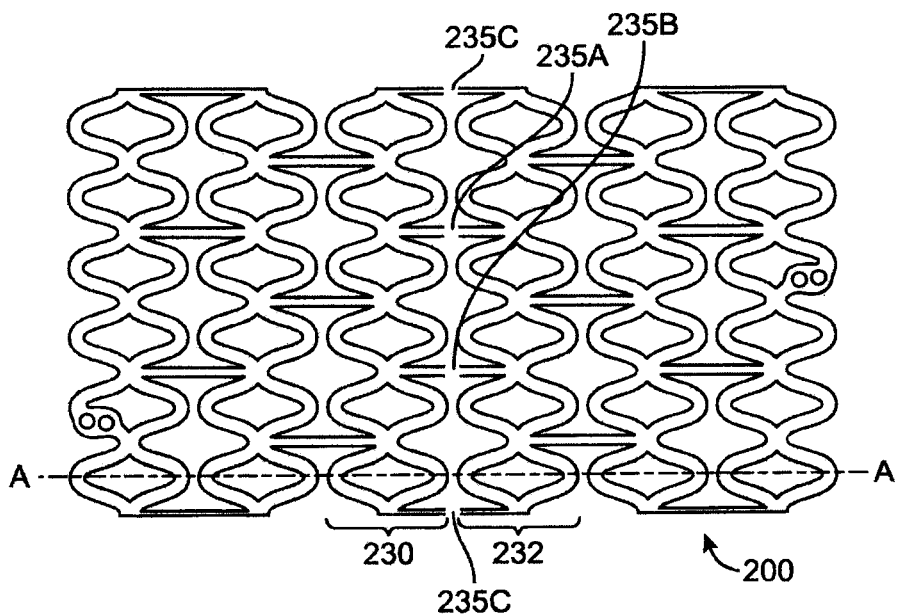
Figure 6:
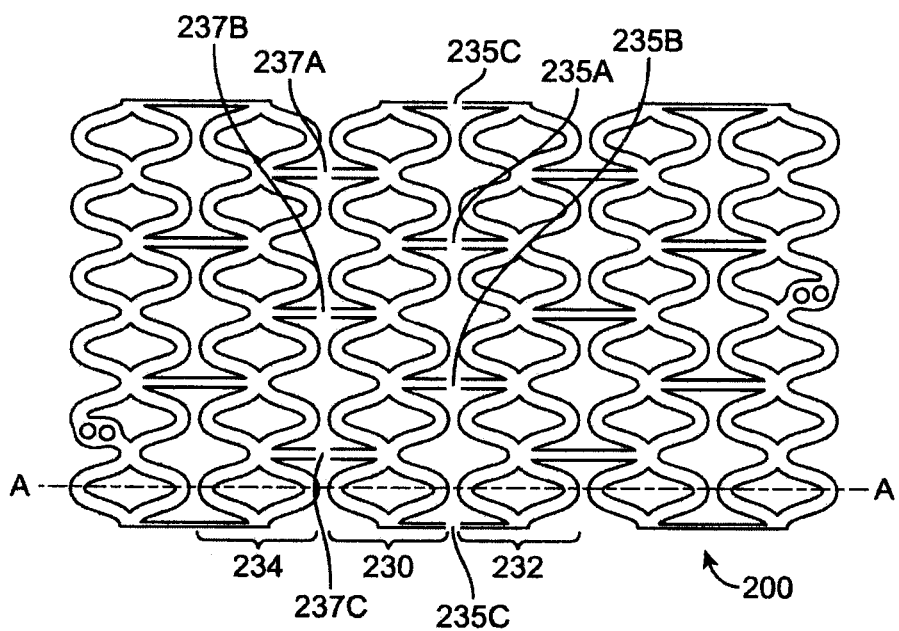
Figure 7:
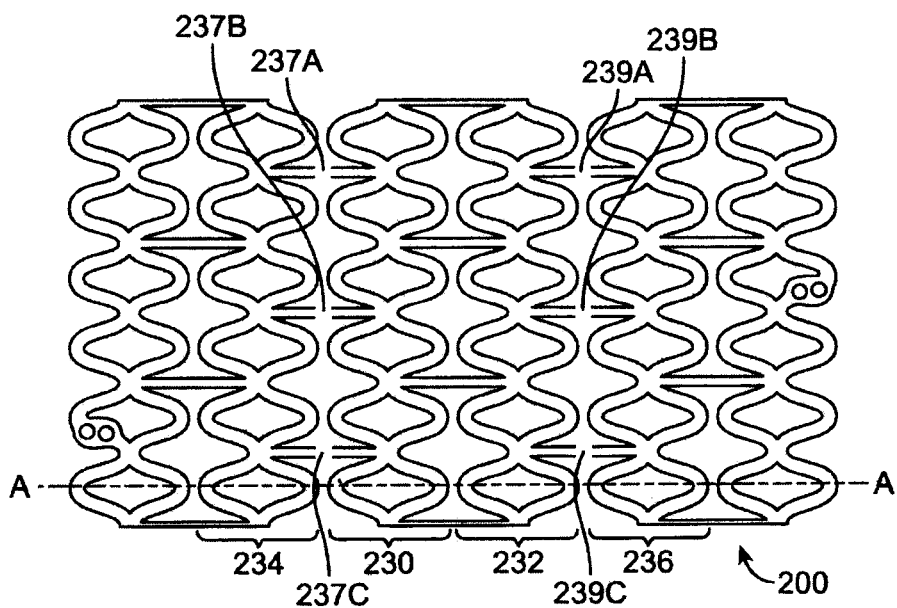
Figure 8:
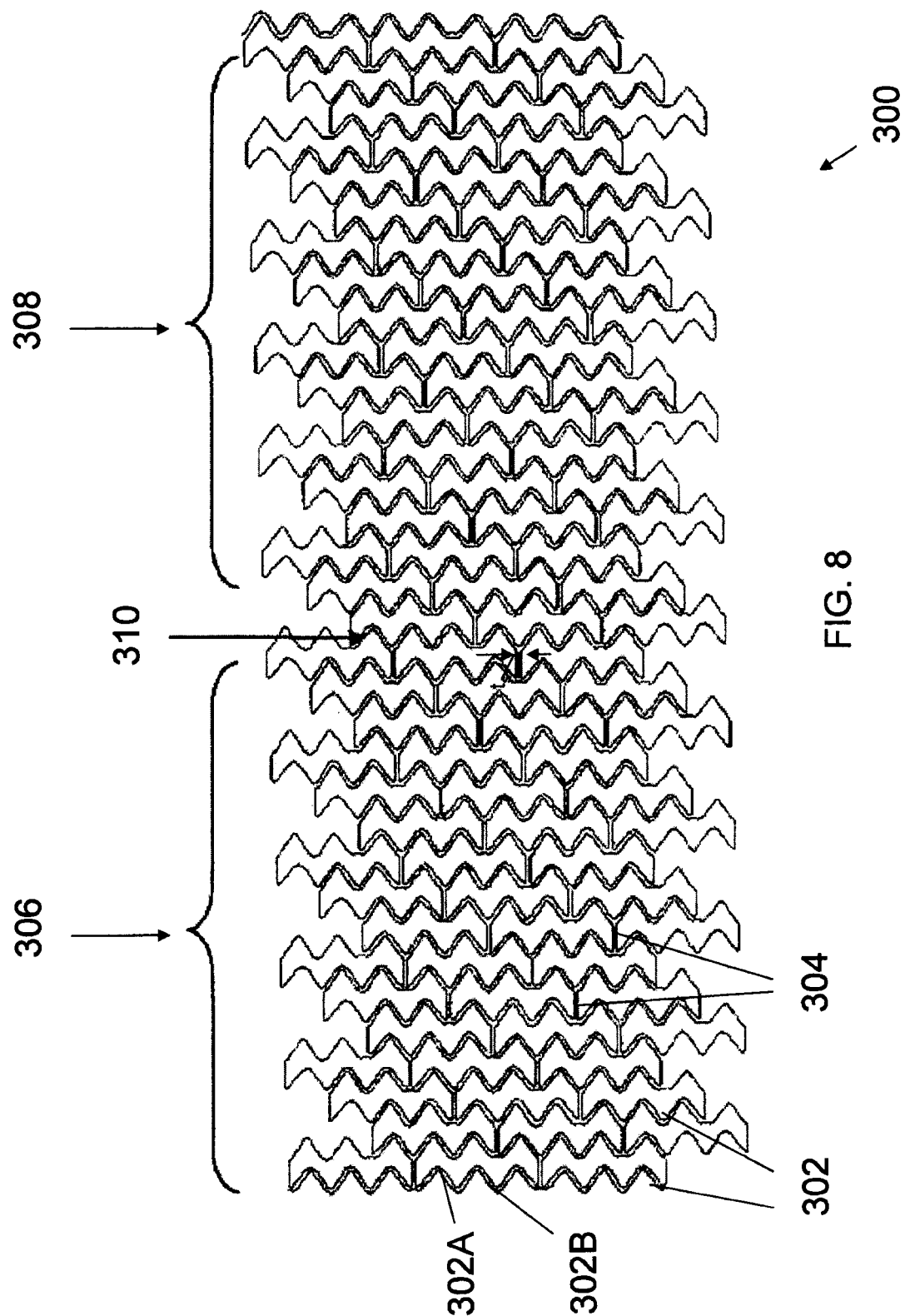
Figure 9A:
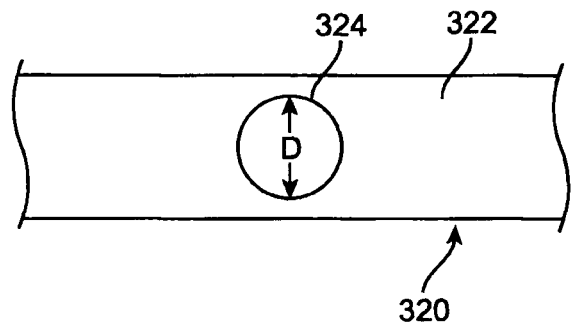
Figure 9B:
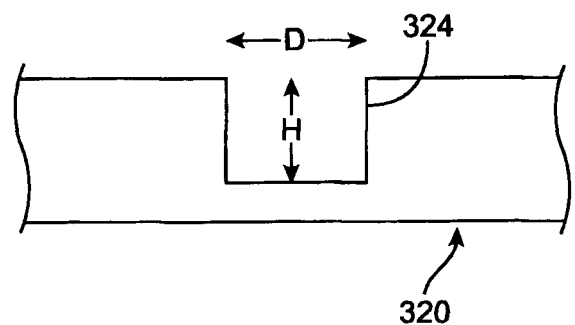

FIG. 3A depicts a two-dimensional projection of a stent 150 deployed in a segment of a vessel with a wall 152. Stent 150 has rings 154, 156, 158, and 160 that are opposed against a vessel wall 152. The rings have linking elements 162, 164, 166, 168 and 170. Linking elements 164, 168, and 170 are designed to fail leaving pairs of rings 154-156 and 158-160 connected. FIG. 3B depicts stent 150 with ring pair 154-156 connected and ring pair 158-160 connected. Ring pairs 154-156 and 158-160 are disconnected due to failure of linking elements 164, 168, and 170 (not shown).

This set of embodiments is useful for maintaining patency in vessels such as the SFA which are subject to significant forces due to compression, torsion, flexion, extension, and contraction. In general, it is particularly useful in vessels that impart stresses on the stent structure that are not radially directed, for example, forces that place stress on the stent along a longitudinal or helical direction. Longitudinal stresses can arise from longitudinal compression and extension, while helical stress can arise from torsional forces. Such stresses are propagated along the length of the stent and can impart significant stress and strain throughout the stent structure. In particular, forces due to compression, torsion, and extension can be transmitted by linking struts connecting rings to the rings, causing failure to the rings. The stresses and strain can be imparted in sections of the structure and along axes that are not designed to be load bearing. Decoupling the rings or sections of rings from one another reduces or eliminates such stress and failure of rings.

Additionally, the embodiments of decoupled rings are advantageous in vessel segments that have a significant degree of curvature. The decoupling of rings reduces or prevents propagation of failure to rings due to bending of the stent structure along its axis. The decoupling also allows individual rings or decoupled sections rings the freedom to orient in a manner that maximizes the support of the lumen, i.e., the opening of a ring coincides more closely with the lumen opening.

The decoupling of the rings is particularly advantageous for treating curved sections of vessels, both coronary and peripheral. Curvature in vessels may arise or be increased from increased physiological demands caused by physical exertion or movement. In this case, the curvature changes with time depending on the level of physical exertion. Additionally, there are sections of vessels that have curvature even in the absence of increased physiological demands. Since the rings are decoupled, the rings fit around or follow the natural curvature of the vessel. The decoupled rings cause minimal or no stress tending to decrease the curvature away from a natural state. The decoupled rings also cause minimal or no stress that tends to inhibit changes in curvature due to physiological demands. When the curvature of the vessel changes with time due to physiological demands, the decoupled rings allow the vessel curvature to change. This is in contrast to a metallic stent that tends to decrease the natural curvature or inhibit changes in curvature which causes additional stress to the section.

The preference for decoupled single rings or sections of rings depends on the degree of non-radially directed forces and the degree of bending of the vessel. The greater the forces, degree of bending, or both, then decoupled single rings or a smaller sections (e.g., pairs of rings) is preferred.

Further embodiments of the present invention include a bioabsorbable stent designed to have selective failure of structural element to provide the controlled loss of mechanical strength described above. In such embodiments, selected structural elements can be designed to fail or break before other structural elements that remain free of fractures or unbroken for a period time. These selected structural elements can be designed to fail at about the same time.

The selected structural elements can be non-load bearing elements, such as linking struts. Some or all of the non-load bearing or linking struts can be designed to fail or break, for example in the manner described above. When the selected structural elements break, the unbroken structural elements, can continue to serve a clinical need, such as rings that provide support to a vessel wall. Additionally or alternatively, the unbroken elements can remain intact until covered by endothelial tissue.

The selected structural elements can have a property or feature that makes the structural elements susceptible to failure sooner than structural elements that are free of the property or feature upon deployment of the stent in a living body. The selected structural elements or regions thereof can be selectively modified to have the property or feature that is different unmodified regions. The property or feature includes, but is not limited to, a coating that accelerates the degradation of a strut, a region of reduced strut cross-section, or a region of reduced molecular weight of the scaffolding polymer.

Figure 4:
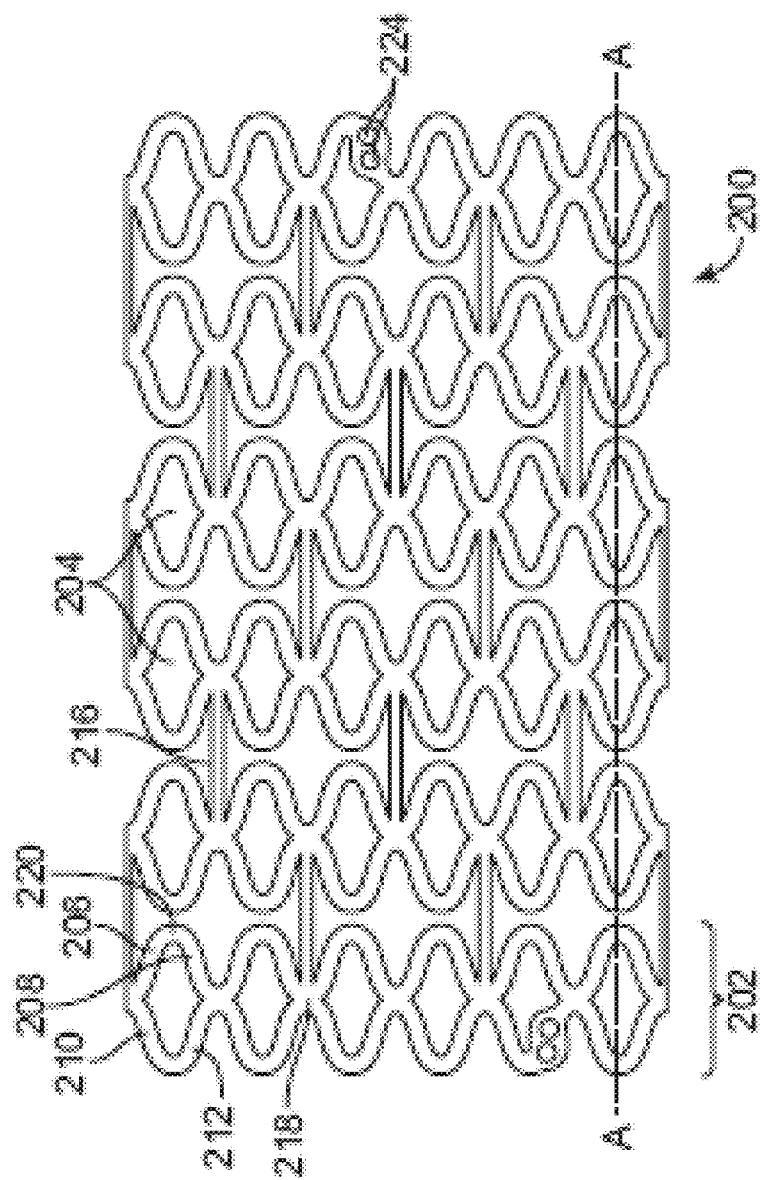
FIG. 4 depicts an exemplary stent pattern for illustrating selective failure of stent struts.

FIG. 4 depicts an exemplary stent pattern 200 for illustrating selective failure of stent struts. Stent pattern 200 is shown in a flattened condition so the pattern can be clearly viewed. When the flattened portion of stent pattern 200 is in a cylindrical form, it forms a radially expandable stent. Stent pattern 200 includes a plurality of cylindrical rings 202 with each ring made up of a plurality of diamond shaped cells 204. Linking struts 216 connect adjacent cylindrical rings. Linking struts 216 are parallel to line A-A and connect adjacent rings between intersection 218 of cylindrically adjacent diamond-shaped elements 204 of one ring and intersection 218 of cylindrically adjacent diamond shaped elements 204 of an adjacent ring.

Stent pattern 200 can have any number of rings 202 depending a desired length of a stent. For reference, line A-A represents the longitudinal axis of a stent using the pattern depicted in FIG. 4. Diamond shaped cells 204 are made up of struts 206 and 208 that form a curved element and struts 210 and 212 that form an opposing curved element. Pattern 200 includes pairs of holes 224 in struts at both ends of the stent to accommodate radiopaque markers.

Figure 5:
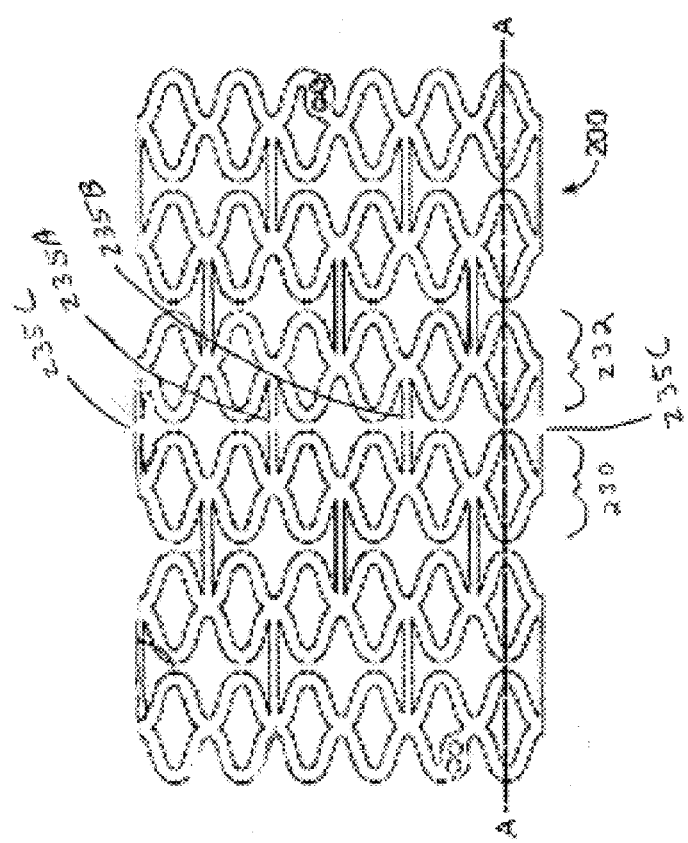
FIGS. 5-7 depict the pattern of FIG. 4 with decoupled rings.

In certain embodiments, the selective failure of structural elements disconnects or decouples at least one pair of adjacent rings. In one embodiment, each of the linking struts that connects a pair of adjacent rings is selectively modified to fail. In FIG. 5, which depicts the pattern of FIG. 4, a pair of adjacent rings, 230 and 232, are decoupled by the selective failure of linking struts 235A, 235B, and 235C. Such a failure results in decoupling the stent into two sets of rings of equal number.

Figure 6:
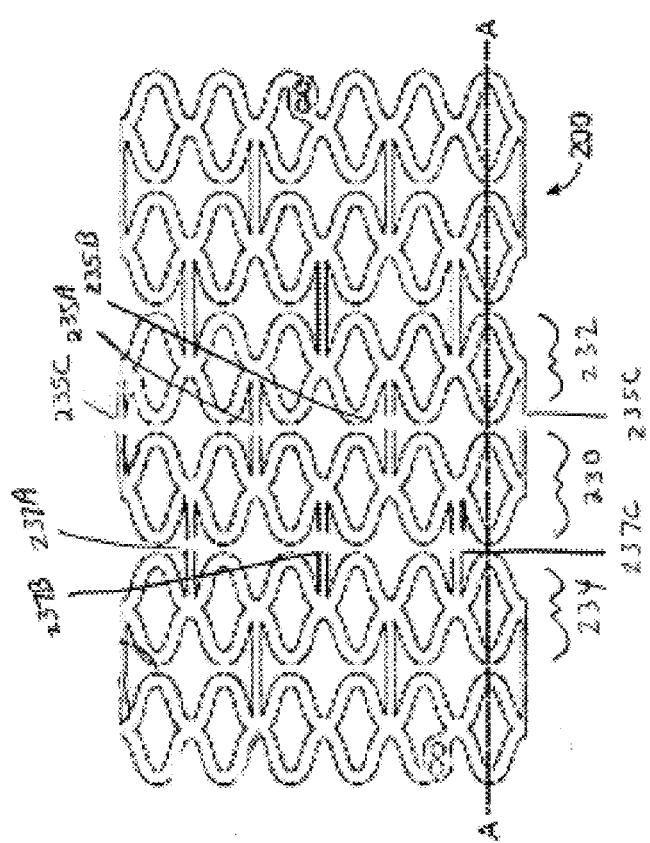

The selective failure can also include decoupling at least one ring or group of consecutive rings completely from adjacent rings. The selected structural elements include all of the linking struts that connect the ring or the consecutive group of rings to adjacent rings. In FIG. 6, ring 230 is decoupled from rings 232 and 234 by the selective failure of linking struts 235A-C and linking struts 237A-C, respectively.

Figure 7:
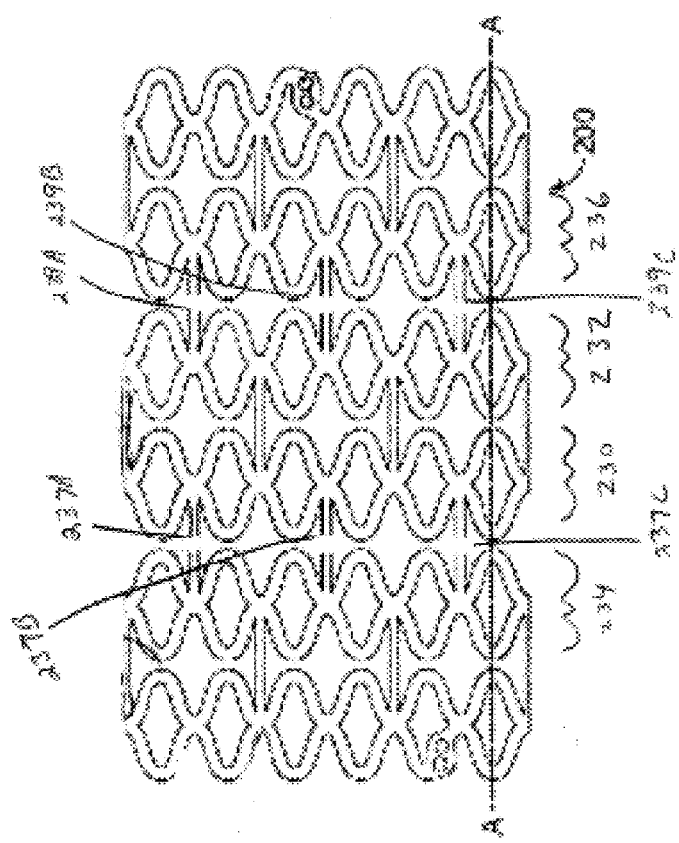

Similarly, referring to FIG. 7, consecutive ring pair 230-232 is decoupled from rings 234 and 236 by failure of linking struts 237A-C and linking struts 239A-C, respectively. In FIG. 6, the stent is broken up into three sets of rings of unequal number, two, one, and three. In FIG. 7, the stent is broken up into three sets of rings of equal number.

The selected failure can also include decoupling all of the rings or all groups of consecutive rings completely. With the pattern of FIG. 5, failure of all of the linking struts would result in eight decoupled rings.

The manner of failure that is desirable depends upon the type and degree of force to which a deployed stent is subjected. As the degree of flexing, torsion and longitudinal compression and extension increases, smaller and more sets of decoupled rings are desirable.

Figure 8:
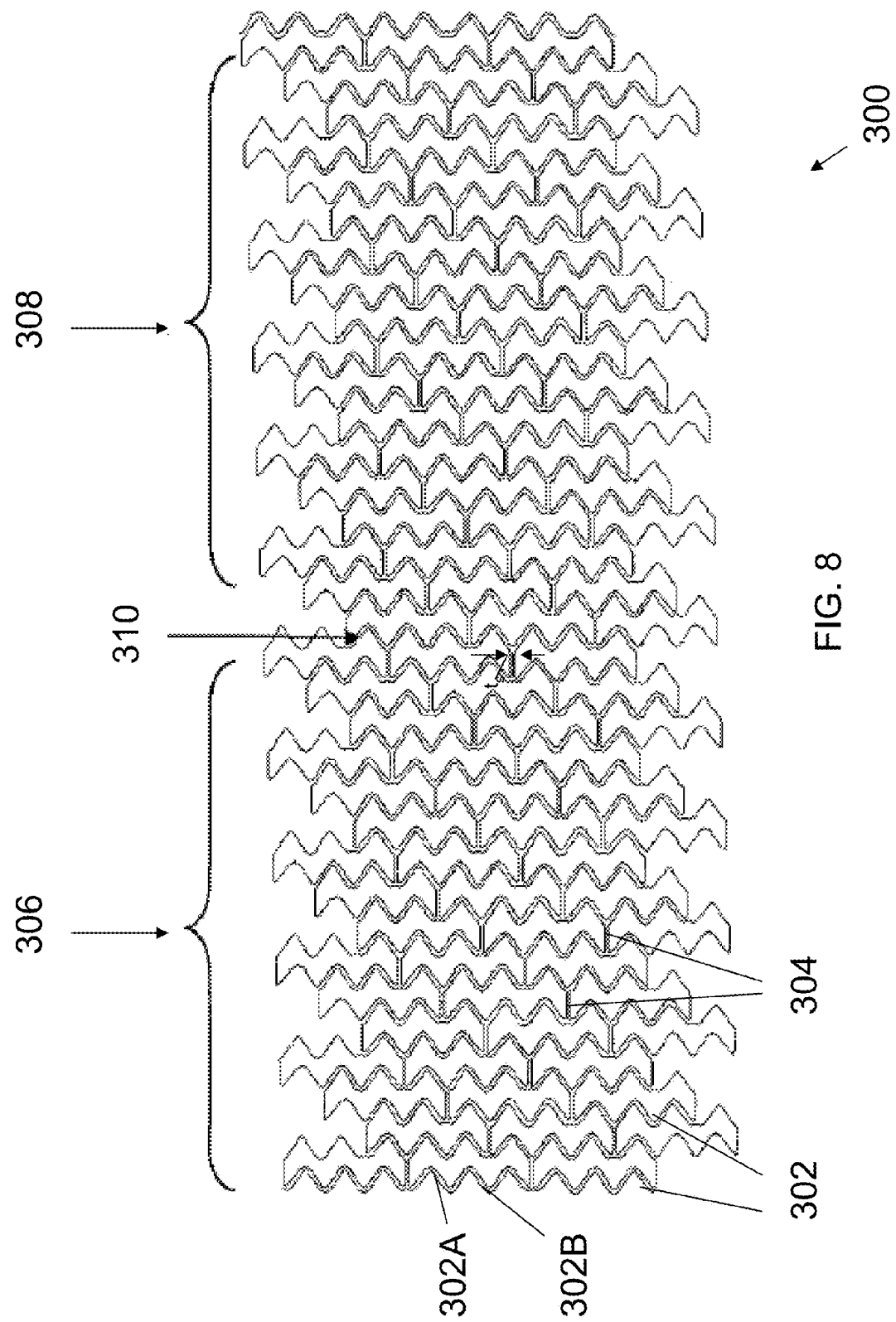
FIG. 8 depicts another exemplary stent pattern for illustrating selective failure of stent struts.

FIG. 8 depicts another exemplary stent pattern 300 for illustrating selective failure of stent struts. Stent pattern 300 is also shown in a flattened condition. Stent pattern 300 includes a plurality of cylindrical rings 302 with each ring made up of a plurality of undulating struts with peaks 302A and valleys 302B. Linking struts 306 connect adjacent cylindrical rings by connecting the valley of one ring to the valley of the adjacent ring.

In certain embodiments, a period of time after implantation in a vessel, a proximal axial portion 306 is designed to decouple or separate from a distal axial portion 308 through selective fracture of linking struts at ring 310. In an exemplary embodiment, the stent can be designed for treatment of the SFA with an exemplary length of about 10 cm or about 15 cm. In one embodiment, weeks or months after implantation, the 10 cm stent separates into two 5 cm sections. In another embodiment, the 15 cm stent can separate into three 5 cm sections.

The linking struts that are designed or preprogrammed to selectively fail prematurely, for example, at ring 310, can have a structure that results in the linking struts to selectively fail or fracture, causing separation of axial sections of the stent. In one embodiment, all of the linking struts at a selected axial location or ring have a thickness, ts, less than linking struts that are not designed to selectively fail prematurely, for example, linking struts in portions 304 and 306. For example, the linking struts can have a thickness that is 0.1 to two thirds the width of linking struts that are not designed to fail prematurely. In some embodiments, all linking struts around a ring can be designed to selectively fail at selected axial locations, for example, every 6 cm±3 cm.

Linking struts can be or preprogrammed to selectively fail prematurely in a number of ways. As discussed above, the struts designed to selectively fail prematurely can have a reduced thickness. In addition to this or as an alternative, the selective failure can be induced or facilitated by increasing the degradation or erosion at the desired fracture points or regions.

The degradation or erosion can be increased at the desired fracture regions by increasing the surface area of the contact points. In one embodiment, holes can be cut at the connection points or regions of the linking struts to the rings. The degradation in such connection points or regions will be increased and the fracture and separation adjacent rings will occur sooner. The holes can have openings in the abluminal surface and be cut by laser machining. The time of failure of the linking struts can be adjusted through variation of the diameter and depth of the holes.

Selective failure of a linking strut can also be induced or facilitated by a hole (e.g., drilled by a laser) in an abluminal surface of the strut away from the connection points or regions. The hole can act as a stress concentrator and increase the degradation rate of the linking strut. The hole can be located at or near the middle of the connector where the bending moment is maximal. The diameter of the hole can be, for example, between 50% to 80% of the width of the strut.

Figures 9A, 9B:
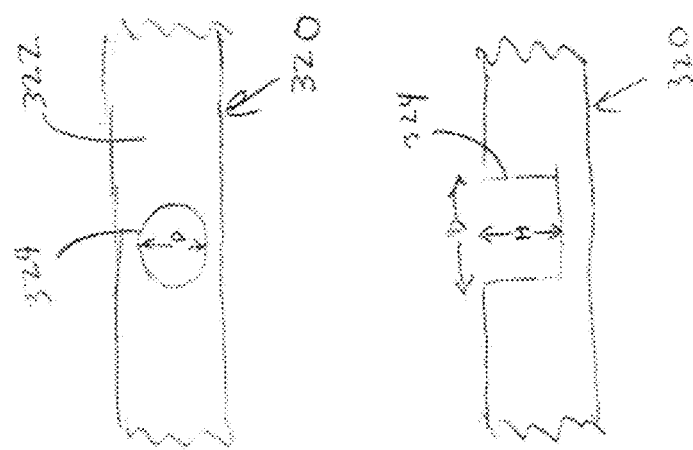
FIG. 9A depicts a view of the abluminal surface of linking strut with a hole.
FIG. 9B depicts a cross-sectional side view of the linking strut of FIG. 9A.

A hole at or away from a connection region can be a through-hole (i.e., all the way through from the abluminal to the luminal surface of the strut) or partially through the thickness of the linking strut (e.g., less than 20%, 40%, 60%, or 80% of the thickness). FIG. 9A depicts an abluminal surface 322 of a linking strut 320 with a hole 324 with a diameter D. FIG. 9B depicts a cross-sectional side view of linking strut 320 showing hole 324 with a depth H.

In addition, the selective failure of the linking struts can be induced or facilitated by a region of reduced cross-section along the linking strut. The regions can act as stress concentrators that facilitate fracture and failure. The regions also increase degradation due to the increased surface area. The susceptibility to failure is related to the thickness and length of the reduced cross-section. The thinner and shorter the length, the more concentrated the stress is at the region and the more likely and sooner it will fail. The region can include one or more notches along a linking strut in the abluminal (outer) surface, luminal surface (inner surface), or sidewalls. The reduced cross-section regions can be formed by laser cutting.

Figure 10A:
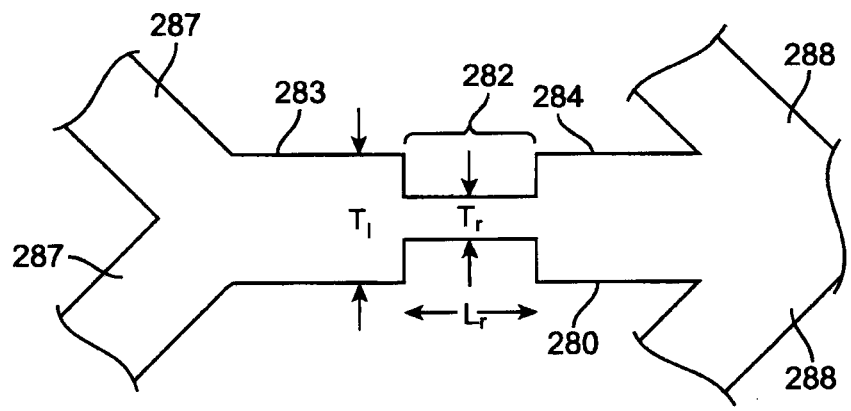
FIG. 10A depicts a linking strut with a reduced cross-section.

FIG. 10A depicts an abluminal surface of a linking strut 280 that is connected to ring struts 287 and 288. Linking strut 280 has a reduced cross-section region 282 between regions 283 and 284. Region 282 has a length Lr and thickness Tr, the thickness Tr being less than a thickness Tl of regions 283 and 284. As Lr and Tr decrease, region 282 becomes more susceptible to fracture.

Figure 10B:
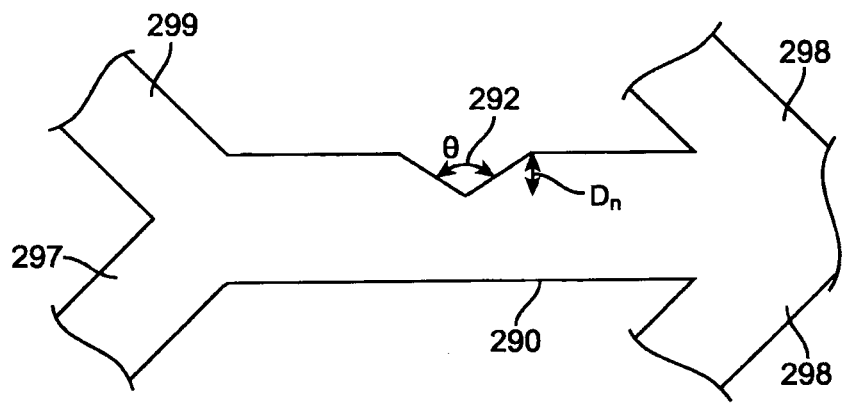
FIG. 10B depicts a linking strut with a notch.
Figure 11:
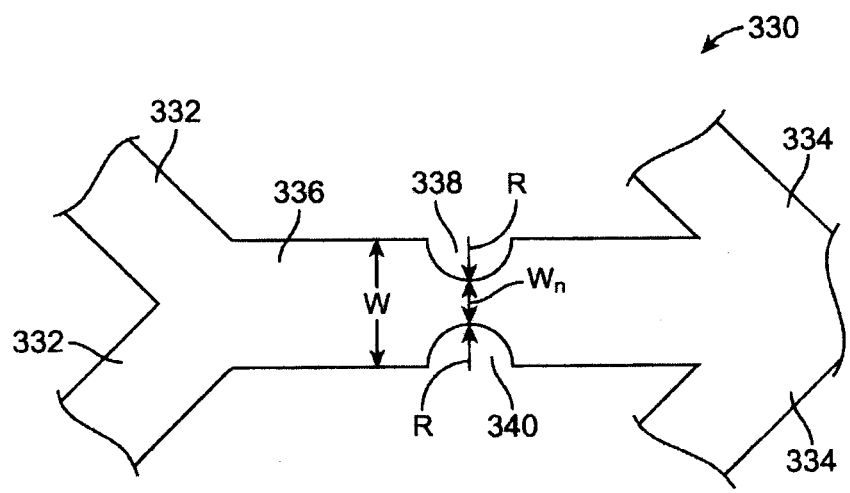
Figure 12A:
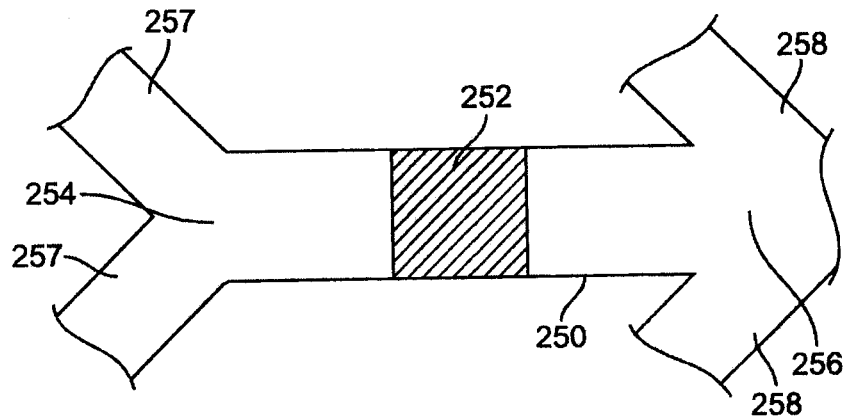
Figure 12B:
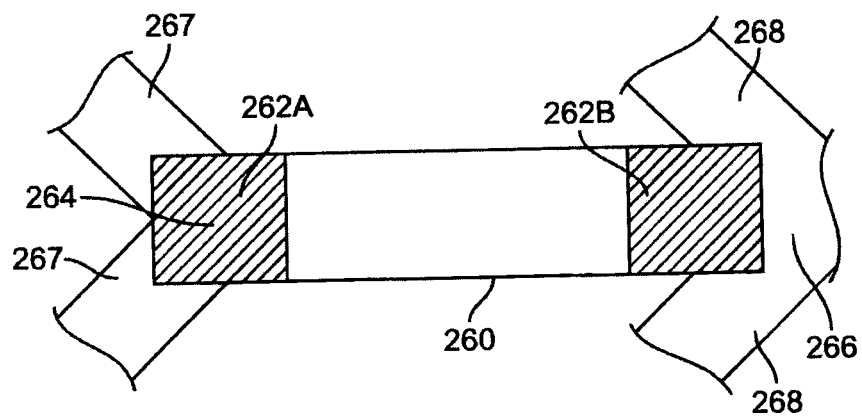

FIG. 10B depicts an abluminal surface of a linking strut 290 that is connected to ring struts 297 and 298. Linking strut 290 has a notch 292 with a depth Dn and angle α. As Dn increases and α decreases, region 292 becomes more susceptible to fracture.

Figure 11:
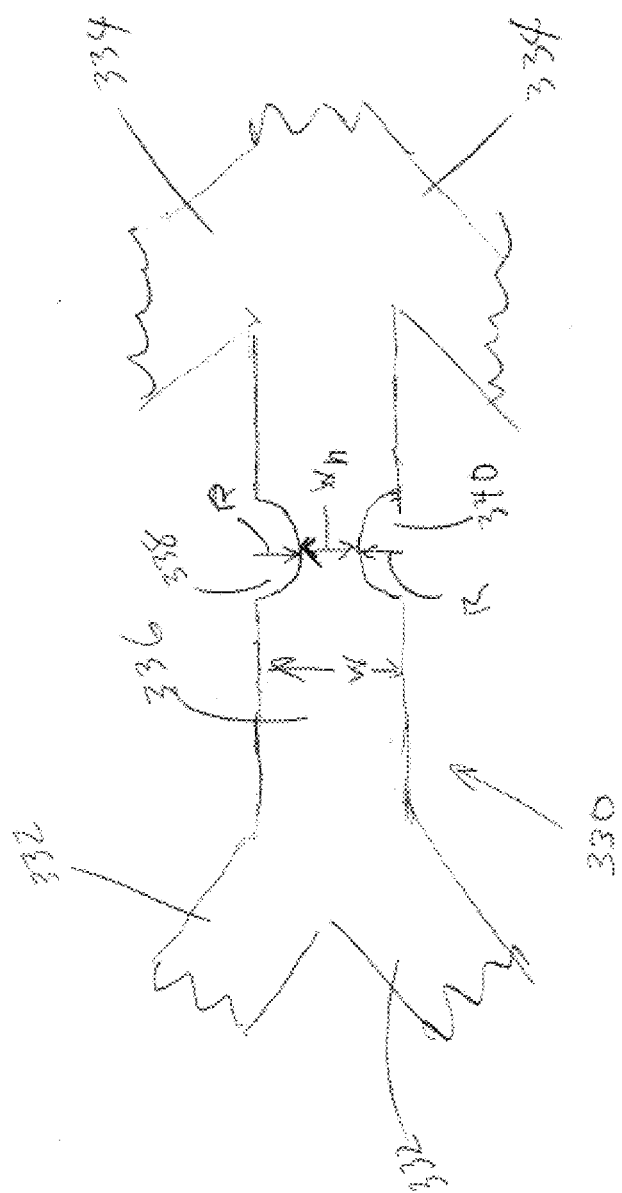
FIG. 11 depicts an abluminal surface of a linking strut with two half circle shaped cavities.

In order facilitate the fracture of the linking struts or specific linking struts, the moment of inertia of a linking strut can be reduced by two opposing half circles-shaped cavities at the edge of the linking strut at or near the middle of its length. FIG. 11 depicts an abluminal surface 336 of a linking strut 330 that is connected to ring struts 332 and 334. Linking strut 330 has two opposing half circle cavities 338 and 340 cut into the side walls of the linking strut. Half circles 338 and 340 have radii R (the radii need not be the same) and the narrowest width of the linking strut between the half circles is Wn. R can be between about 5% and 30% of the width W of the linking strut. R and Wn can be adjusted to obtain desired fracture behavior.

In addition, the creep compliance at a specific link strut region can be reduced selectively by introducing additional crystallinity in a region. The additional crystallinity increases the susceptibility to fracture of the region and thus the linking strut. The additional crystallinity can be introduced by selective annealing of the region. The selective annealing may be performed by selectively heating the region to a temperature between Tg and Tm of the polymer of the strut since crystal nucleation and growth occurs in this temperature range for a semicrystalline polymer. The selective annealing can be used alone or in combination with other modifications of a linking strut which facilitate fracture and failure.

The region that is selectively annealed can be along the entire length of the linking strut, for example, along the abluminal surface of the linking strut. The region can also include the connection point or area of the linking strut to a ring, with one or both connection points electively annealed. Alternatively, only a portion of the linking strut along its length can be selectively annealed, for example, a region near the middle of the linking strut. In addition, a region at or near a structurally modified section of the linking strut can be selectively annealed, such as a notch, region of reduced cross-section, between two half circle-shaped cavities, or holes.

A region can be selectively annealed by selective heating with, for example, a laser or conductive heating element. Representative examples of lasers that may be used include, but are not limited to, excimer, carbon dioxide, and YAG lasers. Conductive heating can be performed with a heated filament and may be disposed proximate to or in contact with a selected region. The increased crystallinity along with a reduced width is a variable that can be program the controlled fracture at a desired time of the stent.

The selective failure of a linking strut can also be caused or facilitated by including a coating over at least a portion of the linking strut that accelerates the degradation of the scaffolding polymer of the linking strut once the stent is implanted.

The other portions of the linking strut and the rings are free of the coating. The portion with the coating degrades faster, and therefore, loses strength faster than the uncoated portions of the stent. Thus, the portion with the coating has a higher susceptibility to fracture and will selectively fail before the uncoated portions. In some embodiments, a therapeutic coating can be disposed over the accelerant coating. The accelerant coating can also be disposed over the therapeutic coating, however, it is preferred that the accelerant be in contact with the scaffolding.

The coating can include a salt, such as sodium chloride or potassium chloride, that accelerates degradation of the scaffolding polymer, an alkali that accelerates degradation of the scaffolding polymer, or an acid such as citric acid, lauric acid etc. that upon hydration can decrease the local pH, therefore, causing faster degradation of the scaffolding polymer. Additionally, the coating can include a polymer that accelerates the degradation of the scaffolding polymer. Such a polymer can include a polymer with a higher degradation rate than the scaffolding polymer. The higher degradation rate can be based, for example, on experimentally observed degradation times of the polymers. These are listed in Table 1 for various types of polymers. For example, a PGA or PLGA coating can accelerate the degradation of a PLLA scaffolding polymer. In another example, racemic PDLA and meso PDLA can be added to modulate the degradation rate of the scaffolding polymer.

Additionally, a polymer with acid-terminated end groups can be used to accelerate the degradation of the scaffolding polymer. For example, the coating can include the scaffolding polymer or another biodegradable polymer with acidic groups. Polymers with acidic end groups can then be synthesized, for example, by reacting polymers with ester end groups with succinic anhydride. For example, PLLA reacts with succinic anhydride in the presence of a stannous octoate catalyst at an elevated temperature to form a PLLA with end groups at each end of the polymer. The succinic anhydride end-caps the PLLA with an acid group.

Figure 12A:
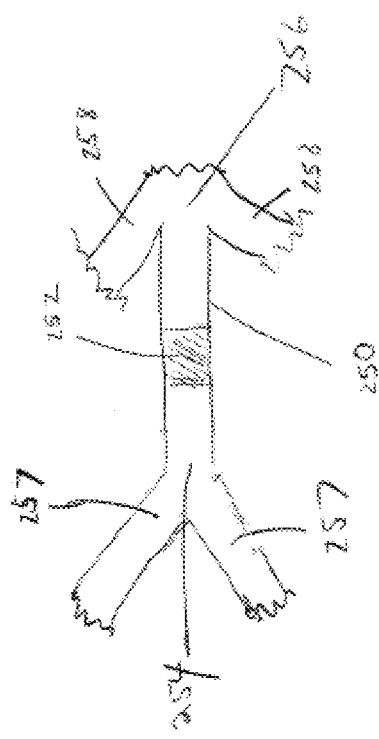
FIGS. 12A-B depicts linking struts with coating regions that accelerate degradation.

As indicated above, the coating can be disposed above a portion of the linking struts. The coating can be disposed above a surface region between the connection at the intersections with the rings, and the rest of the linking strut can be free of the coating. FIG. 12A depicts a linking strut 250 with a coating region 252 above a surface region between the intersections 254 and 256 with a first ring having ring struts 257 and a second ring having ring struts 258, respectively.

Figure 12B:
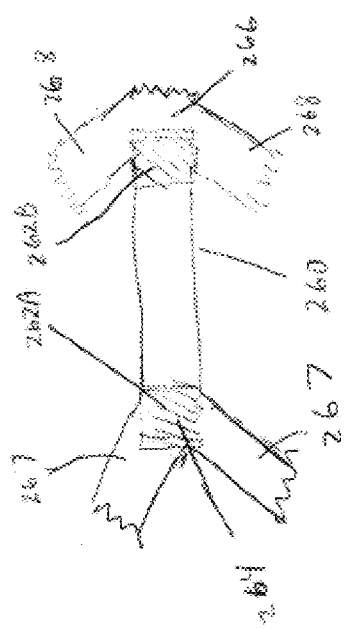
Figure 1:
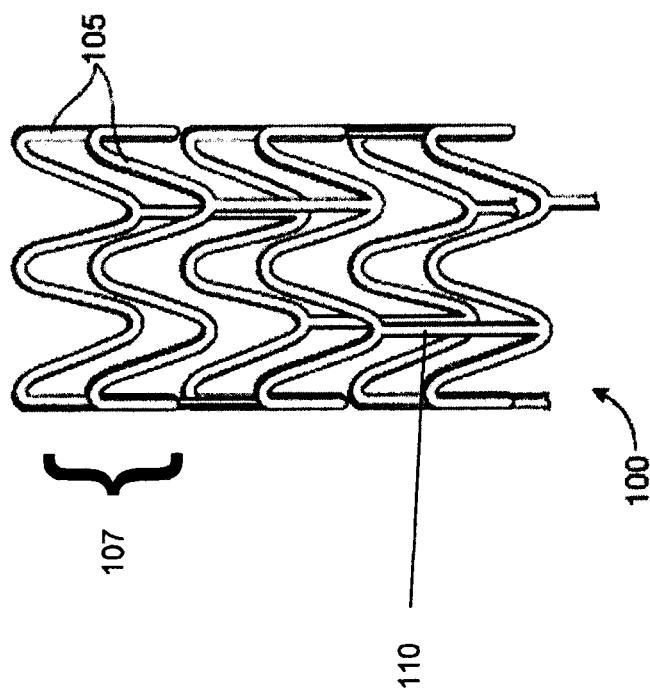
Figure 2A:
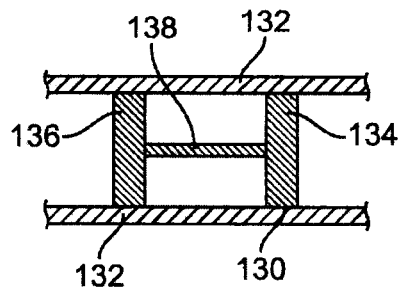
Figure 2B:
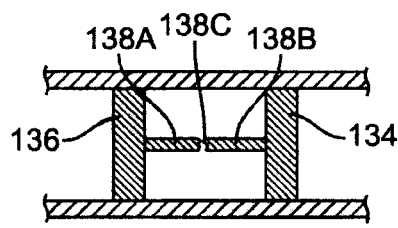
Figure 2C:
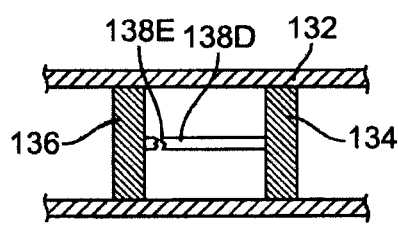

The coating can also be disposed at a surface region at or near one or both of the intersections of the linking strut with the rings, the rest of the linking strut being free of the coating. Due to the intersection, this region can be more susceptible to failure than the portion between intersections. FIG. 12B depicts a linking strut 260 with coating regions 262A and 262B above intersections 264 and 266 with a first ring having ring struts 267 and a second ring having ring struts 268, respectively.

Alternatively, the coating can be disposed along the whole surface of the linking struts. This option can be an advantage since it may cause the strut to fail faster than a strut with coating regions above limited regions. However, a coating over a limited portion of the strut is an advantage since a smaller amount of degradable material may decrease the possibility of an inflammatory response due to the degradation by-products.

The selective coatings of the linking struts may be applied using various methods. Spray coating may be used by placing masks over regions other than the selected regions. Alternatively, controlled deposition systems can be used which can apply various substances only to certain targeted portions of a medical device. A representative example of such a system, and a method of using the same, is described in U.S. Pat. No. 6,395,326 to Castro et al. A controlled deposition system can be capable of depositing a substance on a medical device having a complex geometry, and otherwise apply the substance so that coating is limited to particular portions of the device.

Additionally, the properties of the scaffolding polymer on the linking struts can be selectively modified to induce the selective failure. Some embodiments can include modifying at least a portion of the linking strut to decrease the molecular weight of the scaffolding polymer in the portion. The weight average molecular weight (Mw) and number average molecular weight (Mn) is lower in the modified portion or region as compared to other portions of the scaffolding. The region corresponds to a volume defined by an area of the surface and a certain depth into the surface. The decreased molecular weight in the region results in an earlier loss of strength and ultimately failure of the linking strut at or proximate to the region.

The molecular weight of a region can be modified by exposing the surface of the scaffolding polymer to radiation capable of modifying the molecular weight or molecular weight distribution of the scaffolding polymer. Various kinds of radiation may be used to modify the molecular weight of the scaffolding polymer, including, but not limited to, electron beam (e-beam), ion beam, x-ray, laser, neutron bombardment, reactive ion etching, infrared (IR), plasma, ultraviolet (UV), and radiation between IR and UV. Additionally, molecular weight can be modified by exposure to reactive ion etching, plasma, and ultrasound frequency application. Each of these types of radiation can cause chain scission in polymers which decreases the molecular weight. E-beam can cause chain scission with exposures at least between 5 kGy and 10 kGy. Ion beams can cause chain scission in the range of $4 \times 10^{-14}$ to $1.2 \times 10^{-14}$ ions/cm$^2$. An IR-laser is expected to cause chain scission with a pulse power of 1 W/cm$^2$ for 0.1 seconds. In addition, a laser may be used to modify the molecular weight of a polymer. The power of the laser should be high enough to cause chain scission without vaporizing the polymer. For example, an infra-read laser may be used.

The depth of the modified region of decreased molecular weight depends on the depth of penetration of the radiation which in turn depends on the energy of the radiation and on the material. In general, the depth of penetration depends on the absorption of the material which can be estimated from Beer's Law. Thus the degree molecular weight modification varies with penetration depth since radiation density varies with distance from the incident surface. One of skill in the art can modify the radiation energy to control the depth and degree of modification of a polymer material at a given depth.

The molecular weight modification can be limited to a discrete region or regions along a linking strut, intersections of the linking strut a ring, or can be include the whole linking strut. Exemplary regions of modification are as illustrated in FIGS. 8A-B.

Various methods may be used to selectively expose a region of the linking strut to radiation to decrease its molecular weight. Methods to reduce the molecular weight in a regioselective manner include use of laser illumination, heat, or chemical degradation. In addition to the MW change, the regioselective application will also induce regioselective modulation of viscoelastic properties of the implant. This is achieved primarily by changes in chain orientation status, onset of additional crystallinity due to the annealing effect, changes in the crystalline lamellar orientation, changes in crystaallite size, size distribution, and spatial gradient.

In some embodiments, a dose of radiation, such as laser illumination, can be selectively directed from a radiation source onto a selected region of a polymer surface of a stent to induce molecular weight loss. In such embodiments, a pulse from a laser source is used that has sufficient energy to induce degradation in the selected portion or regions of the stent, but below the intensity necessary to ablate, cut, or otherwise remove the material. Various types of lasers may be used, such as those with pulse widths in the nanosecond, picosecond, or femtosecond ranges. Additionally, various ranges of laser wavelengths may be used. A laser in the ultraviolet light range, such as an excimer laser, would be a good choice for this application since the ultraviolet light from the excimer laser is absorbed by most polymeric materials and would be contained within the illuminated section of the stent.

Additionally, heat can be applied in a regioselective manner by various mechanisms to decrease the molecular weight of a selection region or portion of a stent. In particular, an infrared laser can selectively heat the desired linking sections.

Additionally, heat and radiation can be selectively applied with techniques that include the use of a modified version of a stent coater. Such a stent coater tracks and applies a coating to specific sections of a stent. If the tip of the stent coater is replaced with a heating element or radiation source, then it can apply heat or radiation to a specific region of individual stents. Thus, a system for selectively directing heat or radiation onto a selected region can be adapted from a controlled deposition system that applies various substances only to certain targeted portions of a device, such as a stent. A representative example of such a system described in U.S. Pat. No. 6,395,326 to Castro et al. was mentioned above. A laser machining system for cutting stent patterns can also be adapted to selective heat or radiation exposure of a stent. Systems for laser machining stents have been described in numerous patents including U.S. Pat. Nos. 6,521,865 and 6,131,266.

In additional embodiments, chemical degradation of selected regions of a stent that decreases molecular weight can be achieved as part of the manufacturing process. In such embodiments, a coating is applied to the selected structural elements or regions of the stent which causes chemical degradation, such as hydrolysis to such elements or regions. This results in a stent that has pre-defined portions that are pre-degraded that will bioabsorb faster than the remainder of the stent that has not been coated with such a coating. The coating can be removed at some time prior to deployment of the stent, such as before crimping and packaging.

The pre-degraded sections of the stent may have mechanical properties that are inferior (e.g., lower tensile strength, fracture resistance, and strain to failure) as the remaining sections of the stent. This is so because typically strain to failure, fracture resistance, and tensile strength depend in large part on the molecular weight of the polymeric material. Thus the pre-degraded sections of the stent may be weaker than the remaining elements of the stent and will fail in a preferential manner.

As described in more detail below, the stent can be designed to have uniaxial preferred polymer chain orientation in the circumferential direction induced through radial expansion of a tube prior to forming a stent pattern. The stent can also have biaxial orientation through axial elongation of the tube. Preferential failure of linking elements at the linking element-ring junction or at another point along the linking element can be induced by having the circumferential strength sufficiently greater than the strength transverse to the circumferential direction. This can be achieved by greater polymer chain orientation in the circumferential direction than the transverse direction. The stent of the can be made from variety of biodegradable polymers including, but not limited to, poly(L-lactide) (PLLA), polymandelide (PM), poly(DL-lactide) (PDLLA), polyglycolide (PGA), polycaprolactone (PCL), poly(trimethylene carbonate) (PTMC), polydioxanone (PDO), poly(4-hydroxy butyrate) (PHB), and poly(butylene succinate) (PBS). The stent can also be made from random and block copolymers of the above polymers, in particular, poly(L-lactide-co-glycolide) (PLGA) and poly(L-Lactide-co-caprolactone) PLGA-PCL. The stent can be made from PLGA including any molar ratio of L-lactide (LLA) to glycolide (GA). In particular, the stent can be made from PLGA with a molar ratio of (LA:GA) including 85:15 (or a range of 82:18 to 88:12), 95:5 (or a range of 93:7 to 97:3), or commercially available PLGA products identified as having these molar ratios. Table 1 provides properties of some of the above-mentioned polymers. High strength, semicrystalline polymers with a Tg above body temperature include PLLA, PGA, and PLGA. High fracture toughness polymers include PCL, PTMC, PDO, PHB, and PBS.

TABLE 1

Properties of biodegradable polymers.

| Polymer | Glass-Transition Temp (° C.)[1] | Modulus (Gpa) | Tensile Strength (Mpa) | Elongation at break (%) | Degradation Time (months)[a] |
|---|---|---|---|---|---|
| PGA | 35-40 | 7.0[1]<br>5-7[2] | 60-80[2] | 30[4] | 6-12[1,2] |
| PLLA | 60-65 | 2.7[1]<br>3[2] | 60-70[2] | 3[4] | >24[1]<br>>36[2] |
| PDLLA | 55-60 | 1.9[1]<br>2[2] | 2[2] | N/A | 12-16[1]<br>12-15[2] |
| PCL | (−65)-(−60) | 0.4[1,2]<br>0.386[4] | 20-25[2]<br>4[4] | 800-1000[4] | >24[1]<br>>36[2] |
| PDO | (−10)-0 | 1.5[1,2] | 30[2] | 35[3] | 6-12[1]<br>6[2] |
| PHB | N/A | 4[4] | 40[4] | 6[4] | |
| PGA-TMC | N/A | 2.4[1] | N/A | N/A | 6-12[1] |
| 85/15 PLGA | 50-55[1] | 2.0[1] | N/A | N/A | 5-6[1] |
| 75/25 PLGA | 50-55[1] | 2.0[1] | N/A | N/A | 4-5[1] |
| 65/35 PLGA | 45-50[1] | 2.0[1] | N/A | N/A | 3-4[1] |

TABLE 1-continued

Properties of biodegradable polymers.

| Polymer | Glass-Transition Temp (° C.)[1] | Modulus (Gpa) | Tensile Strength (Mpa) | Elongation at break (%) | Degradation Time (months)[a] |
|---|---|---|---|---|---|
| 50/50 PLGA | 45-50[1] | 2.0[1] | N/A | N/A | 1-2[1] |

[1]Medical Plastics and Biomaterials Magazine, March 1998.
[2]Medical Device Manufacturing & Technology 2005.
[3]The Biomedical Engineering Handbook, Joseph D. Bronzino, Ed. CRC Press in Cooperation with IEEE Press, Boca Raton, FL, 1995.
[4]Science, Vol. 297 p. 803 (2002)
[a]Degradation time also depends on part geometry.

Generally, a high strength, semicrystalline polymer with a Tg above body temperature is a preferred material for a stent scaffolding that can help provide the time dependent behavior discussed above. A semicrystalline polymer generally is composed of crystalline regions or crystallites dispersed in an amorphous matrix. The properties related to the semicrystalline nature of the polymer allow the adjustment of the strength and fracture toughness of the polymer. Specifically, the degree of crystallinity and size of crystallites can be used to adjust strength and fracture toughness. The strength increases with degree of crystallinity and smaller dispersed crystallites enhance the fracture toughness. The small dispersed crystallite microstructure can be imparted to a tube by processing at lower temperatures closer to Tg, for example, during a radial expansion process.

In the first set of embodiments described above, the stent is designed to have a high fracture toughness in addition to high radial strength. A polymer material with a high radial strength such as PLLA, PGA, or PLGA, can be used. The polymer can be processed, as described below, with processing that provides high fracture toughness. PGA may be particularly useful due its higher fracture toughness, as shown by its high elongation at break. Additionally, copolymers of PLLA, PGA, or PLGA and a higher toughness polymer such as PCL or PDO can also be used as a high strength and high fracture toughness material. The copolymers can be block or random copolymers.

The degree of crystallinity is limited to a range of about 10-40%. A higher degree of crystallinity will increase the strength, however, can reduce the fracture toughness and result in brittle behavior. Additionally, the polymer tube from which the stent is made is radially expanded, which increases its strength and crystallinity. Prior to expansion, the tube is heated to a temperature between Tg and Tm in a range close to Tg to induce formation of smaller crystallites that enhance fracture toughness. The tube is quenched below Tg after deformation to prevent further crystal growth. The percent radial expansion is between 200 and 500%. Additionally, the polymer of the stent can include plasticizer to enhance the fracture toughness.

In the second set of embodiments, the stent is designed to have a higher radial strength and lower fracture toughness. The polymer material can include, for example, PLLA, PGA, or PLGA.

As above, the stent is made from a tube that is radially expanded. The percent radial expansion can be greater than above and can be between 200 and 800%. The tube can be processed to induce a higher degree of crystallinity to provide higher radial strength. The degree of crystallinity may be, for example, between 40-50% or 50-70%. The tube can be heated to a similar temperature above Tg, as above, prior to deformation. However, the tube can be annealed prior to deformation, after deformation, or both to increase the crystallinity.

The fabrication methods of a bioabsorbable stent for use in the methods of treatment described herein can include the following steps:
(1) forming a polymeric tube using extrusion,
(2) radially deforming the formed tube,
(3) forming a stent scaffolding from the deformed tube by laser machining a stent pattern in the deformed tube with an ultra-short pulse laser,
(4) forming a therapeutic coating over the scaffolding,
(5) crimping the stent over a delivery balloon, and
(6) sterilization with e-beam radiation.

The stent scaffolding may be formed from a semicrystalline polymer, as described above. In particular, a semicrystalline polymer has a Tg greater than human body temperature (about 37° C.) so that the scaffolding is rigid after implantation which allows the scaffolding to provide support without excessive recoil.

The mechanical properties of the stent polymer are modified by applying stress to a polymer. In particular, the strength of a polymer can be increased along the direction of the applied stress. Without being limited by theory, the application of stress induces preferred molecular orientation along the direction of stress which increases the strength. Molecular orientation refers to the relative orientation of polymer chains along a longitudinal or covalent axis of the polymer chains.

The fabrication of the polymeric stent includes radially expanding an extruded polymeric tube about its cylindrical axis. Radial expansion deforms the tube circumferentially which increases the radial strength of the tubing, and the subsequently a stent fabricated from the expanded tube. The increase in strength is due to the induced polymer orientation in the circumferential direction. The inventors have also found that the deformation increases the fracture toughness of the stent. Both the increase in radial strength and fracture toughness are important to the ability of the stent to heal a diseased segment of a blood vessel.

Additionally, the stent can have a biaxially oriented polymer structure. To achieve this, the tube is axially deformed to provide increased strength in the axial direction, in addition to being radially expanded. For example, the tube may be axially deformed by applying a tensile force to the tube along its cylindrical axis.

Since the tube is heated to a temperature above Tg for the deformation, the degree of crystallinity is increased as the tube is heated and deformed, due to stress-induced crystallization. A microstructure of a high nucleation density and small crystallites provides a higher fracture toughness. Therefore, the tube is heated and deformed in a temperature range that favors a high nucleation density and smaller crystallites. The high density of crystallites that are formed behave as crosslink or tie points that inhibit crack formation and propagation. This range generally corresponds to temperatures closer to Tg than Tm where the nucleation rate is faster than the crystal growth rate. The range depends on the particular type of polymer, however, approximately corresponds to a temperature less than $Tg+0.6\times(Tm-Tg)$, where Tm is the melting temperature of the polymer. For an exemplary polymer, PLLA, which has a Tg of about 60° C., the polymer can be heated to a temperature between 65-120° C. during deformation. Deforming at such low temperatures favors a high nucleation density and smaller crystals, which provides high fracture toughness.

The radial expansion of the polymer tube can be accomplished by a blow molding process. In such a process, the polymer tube is disposed within a cylindrical mold with a diameter greater than the polymer tube. The polymer tube is heated to the temperature range described above. The pressure inside of the tube is increased by blowing a gas into the tube to cause radial expansion of the tube so the outside surface of the tube conforms to the inside surface of the mold. The polymer tube can be axially deformed by a tensile force along the tube axis before, during, and/or after the radial deformation. In some instances, only sufficient tension is applied to maintain the length of the tube as it is expanded. The polymer tube is than cooled below Tg and further processing steps can then be performed, such as laser machining of the tube to form a stent pattern.

The crystallinity imparted to the tube by the radial expansion process depends on the temperature history before, during, and after the expansion. The degree of crystallinity imparted can be minimized by a rapid heating to a deformation temperature and rapid cooling to below Tg after deformation. The degree of crystallinity can be increased by slow heating or slow cooling. Additionally, the degree of crystallinity can be increased by annealing the tube at a temperature above Tg before or after deformation.

The tube is expanded to a target diameter and the stent pattern can be cut into the tube with laser machining at the target diameter. The target diameter can also correspond to the diameter of a stent prior to crimping.

The degree of radial deformation may be quantified by percent radial expansion:

$$\left[\frac{\text{Inside Diameter of Deformed Tube}}{\text{Original outside Diameter of Tube}} - 1\right] \times 100\%$$

In an exemplary embodiment, the percent radial expansion is about 300%. Similarly, the degree of axial deformation may be quantified by the percent axial elongation:

$$\left[\frac{\text{Length of Deformed Tube}}{\text{Original Length of Tube}} - 1\right] \times 100\%$$

The percent axial elongation can be 20-100%.

Axial polymer orientation is also imparted to a tube during formation of the tube as the polymer is drawn out of a die during the extrusion process. The degree of axial orientation of a polymer provided by the draw down process is related the axial drawn down ratio:

$$\frac{\text{Inside Diameter of Die}}{\text{Original Inside Diameter of Tube}}.$$

In an exemplary embodiment the axial drawn down ratio is 2:1 to 6:1.

The stent pattern is formed in the tube with an ultrashort-pulse laser. "Ultrashort-pulse lasers" refer to lasers having pulses with pulse durations shorter than about a picosecond ($=10^{-12}$). Ultrashort-pulse lasers can include both picosecond and femtosecond ($=10^{-15}$) lasers. The stent pattern is formed with a laser with a pulse width less than 200 fs. In an exemplary embodiment, the pulse width used is 120 fs. The use of a femtosecond laser reduces or eliminates damage to polymer material that is uncut and forms the structure of the stent scaffolding.

As discussed above, prior to delivery into the body a stent is compressed or crimped onto a catheter so that it can be inserted into small vessels. Once the stent is delivered to the treatment site, it can be expanded or deployed at the treatment site.

The bioabsorbable stent is heated and crimped above ambient temperature. Heating a stent during crimping can reduce or eliminate radially outward recoiling of a crimped stent which can result in an unacceptable profile for delivery. In an exemplary embodiment, a bioabsorbable stent is crimped at a temperature between 28 and 50° C.

A crimping device can apply pressure and heat simultaneously. In these or other embodiments, after crimping, the crimping device can hold the stent at an elevated temperature, which may be selected such that it is greater than, equal to, or less than the selected crimping temperature or may be selected to specifically exclude temperatures greater than, equal to, or less than the selected crimping temperature. In some embodiments, the device crimps the polymeric stent while the stent is heated by other means.

The crimped stent is further packaged and sterilized. The stent is sterilized through exposure to an electron beam (e-beam). The range of exposure is between 25 and 30 kGy. The radiation exposure causes degradation in the polymer, particularly the molecular weight. As discussed above, the radial strength, mechanical integrity, and erosion profiles are influenced by the molecular weight. To reduce this degradation, the stent is sterilized after reducing its temperature below 0° C. by, for example, placing the stent in a freezer. Additionally, the initial molecular weight and dose are selected to obtain the necessary molecular weight for proper functioning of the stent.

"Radial strength" of a stent is defined as the pressure at which a stent experiences irrecoverable deformation.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that result from the applied force. For example, a material has both a tensile and a compressive modulus.

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

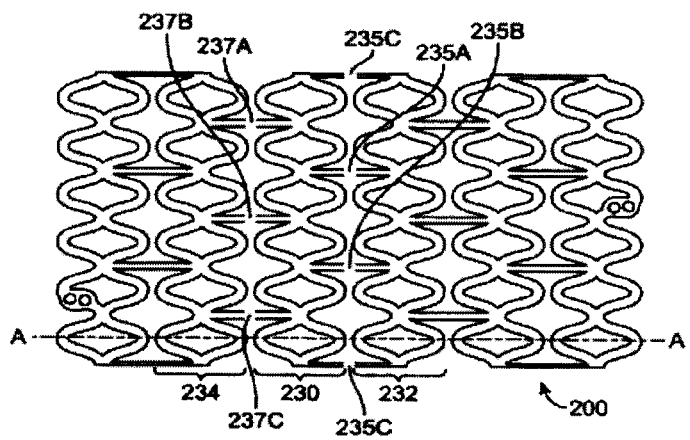

What is claimed is:

1. A method of treating a diseased section of a blood vessel, comprising:

deploying a bioabsorbable polymeric stent to a deployment diameter at a diseased section of a blood vessel to form a stented segment of the vessel comprising the stent and the vessel wall, the stent comprising a scaffolding composed of a pattern of struts, the pattern comprising a plurality of cylindrical rings connected by linking struts, wherein each ring is made up of a plurality of undulating struts with peaks and valleys and which bend to cause plastic deformation at the peaks and valleys when the stent is deployed to the deployment diameter, wherein selected linking struts break after deployment of the stent to the deployment diameter resulting in at least one ring or at least one group of consecutive rings being disconnected from adjacent rings, and wherein the at least one ring or the group of rings remain structurally intact after the selected linking struts break, wherein the selected linking struts break after the stent can no longer support the vessel wall at or near the deployment diameter.

* * * * *

UNITED STATES PATENT AND TRADEMARK OFFICE
CERTIFICATE OF CORRECTION

PATENT NO. : 8,425,587 B2
APPLICATION NO. : 12/561971
DATED : April 23, 2013
INVENTOR(S) : Trollsas et al.

It is certified that error appears in the above-identified patent and that said Letters Patent is hereby corrected as shown below:

The Title page, showing the illustrative figure, should be deleted and substitute therefor the attached Title page.

In the Drawings:

Delete figs. 1, 2A, 2B, 2C, 3A, 3B, 4, 5, 6, 7, 8, 9A, 9B, 10A, 10B, 11, 12A, and 12B and substitute therefor the drawing sheets, consisting of figs. 1, 2A, 2B, 2C, 3A, 3B, 4, 5, 6, 7, 8, 9A, 9B, 10A, 10B, 11, 12A, and 12B as shown on the attached pages.

Signed and Sealed this
Twenty-third Day of July, 2013

Teresa Stanek Rea
*Acting Director of the United States Patent and Trademark Office*

CERTIFICATE OF CORRECTION (continued)

(12) United States Patent
Trollsas et al.

(10) Patent No.: US 8,425,587 B2
(45) Date of Patent: Apr. 23, 2013

(54) METHOD OF TREATMENT WITH A BIOABSORBABLE STENT WITH TIME DEPENDENT STRUCTURE AND PROPERTIES AND REGIO-SELECTIVE DEGRADATION

(75) Inventors: Mikael Trollsas, San Jose, CA (US); Dariush Davalian, San Jose, CA (US); Michael Huy Ngo, San Jose, CA (US); Hao-Ming Hsiao, Cupertino, CA (US); Boris Anukhin, San Jose, CA (US); Syed F. A. Hossainy, Fremont, CA (US); David C. Gale, Kennesaw, GA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 542 days.

(21) Appl. No.: 12/561,971

(22) Filed: Sep. 17, 2009

(65) Prior Publication Data
US 2011/0066225 A1 Mar. 17, 2011

(51) Int. Cl.
*A61F 2/82* (2006.01)

(52) U.S. Cl.
USPC ........................................ 623/1.16; 623/1.38

(58) Field of Classification Search ............... 623/1.38, 623/1.13–1.16; 606/108, 198; 424/426
See application file for complete search history.

(56) References Cited

U.S. PATENT DOCUMENTS

| | | | |
|---|---|---|---|
| 5,486,546 A | 1/1996 | Mathiesen et al. | |
| 5,707,385 A | 1/1998 | Williams | |
| 5,919,893 A | 7/1999 | Roby et al. | |
| 5,972,027 A | 10/1999 | Johnson | |
| 6,174,329 B1 | 1/2001 | Callol et al. | |
| 6,258,117 B1 * | 7/2001 | Camrud et al. | 623/1.16 |
| 7,169,178 B1 | 1/2007 | Santos et al. | |
| 7,175,873 B1 | 2/2007 | Roorda et al. | |
| 7,294,146 B2 * | 11/2007 | Chew et al. | 623/1.12 |
| 7,357,942 B2 * | 4/2008 | Burke et al. | 424/423 |
| 7,625,401 B2 * | 12/2009 | Clifford et al. | 623/1.38 |
| 2001/0044651 A1 * | 11/2001 | Steinke et al. | 623/1.16 |
| 2002/0065553 A1 | 5/2002 | Weber et al. | |
| 2002/0111590 A1 | 8/2002 | Davila et al. | |
| 2003/0040771 A1 * | 2/2003 | Hyodoh et al. | 606/200 |
| 2003/0040772 A1 | 2/2003 | Hyodoh et al. | |
| 2003/0083740 A1 | 5/2003 | Pathak | |
| 2003/0181973 A1 | 9/2003 | Sahota | |
| 2003/0199969 A1 * | 10/2003 | Steinke et al. | 623/1.16 |
| 2004/0034409 A1 | 2/2004 | Heublein et al. | |

(Continued)

FOREIGN PATENT DOCUMENTS

JP 2003-251680 9/2003

OTHER PUBLICATIONS

Loo et al., "Radiation effects on poly(lactide-co-glycolide) and poly-l-lactide", Polymer degradation and stability vol. 83, pp. 259-265 (2005).

(Continued)

*Primary Examiner* — Elizabeth Houston
(74) *Attorney, Agent, or Firm* — Squire Sanders (US) LLP

(57) ABSTRACT

A bioabsorbable polymeric stent with time dependent structure and properties and methods of treating a diseased blood vessel with the bioabsorable polymeric stent are disclosed. The structure and properties of the stent change with time and allow the vessel to be restored to a natural unstented state. The bioabsorbable stent loses mechanical integrity in a controlled manner due to modification of selected structural elements.

1 Claim, 12 Drawing Sheets